(12) United States Patent
Kim et al.

(10) Patent No.: US 10,307,383 B2
(45) Date of Patent: Jun. 4, 2019

(54) COSMETIC COMPOSITION FOR PREVENTING OR AMELIORATING HYPERSENSITIVE SKIN COMPRISING CEDROL OR DERIVATIVES THEREOF, OR PHARMACEUTICALLY ACCEPTABLE SALTS THEREOF

(71) Applicant: University of Seoul Industry Cooperation Foundation, Seoul (KR)

(72) Inventors: Ha Won Kim, Seoul (KR); Dong Hee Lee, Seongnam-si (KR)

(73) Assignee: UNIVERSITY OF SEOUL INDUSTRY COOPERATION FOUNDATION, Seoul (KR)

( * ) Notice: Subject to any disclaimer, the term of this patent is extended or adjusted under 35 U.S.C. 154(b) by 0 days.

(21) Appl. No.: 15/945,601

(22) Filed: Apr. 4, 2018

(65) Prior Publication Data
US 2018/0289634 A1   Oct. 11, 2018

(30) Foreign Application Priority Data

Apr. 5, 2017 (KR) ......................... 10-2017-0044176
Jun. 16, 2017 (KR) ......................... 10-2017-0076435

(51) Int. Cl.
| | | |
|---|---|---|
| A61K 31/045 | (2006.01) | |
| A61K 31/015 | (2006.01) | |
| A61P 17/06 | (2006.01) | |
| A61P 17/04 | (2006.01) | |
| A61P 37/00 | (2006.01) | |
| A61K 31/075 | (2006.01) | |
| A61K 31/12 | (2006.01) | |
| A61K 31/215 | (2006.01) | |
| A61K 31/336 | (2006.01) | |

(52) U.S. Cl.
CPC .......... *A61K 31/045* (2013.01); *A61K 31/015* (2013.01); *A61K 31/075* (2013.01); *A61K 31/12* (2013.01); *A61K 31/215* (2013.01); *A61K 31/336* (2013.01); *A61P 17/04* (2018.01); *A61P 17/06* (2018.01); *A61P 37/00* (2018.01)

(58) Field of Classification Search
CPC ...... A61K 31/222; A61K 31/045; A61P 17/00
See application file for complete search history.

(56) References Cited

U.S. PATENT DOCUMENTS

| | | | | |
|---|---|---|---|---|
| 5,200,429 A | * | 4/1993 | Sato | A61K 31/015 514/766 |
| 6,974,596 B2 | * | 12/2005 | Iwase | A61K 8/0216 424/725 |
| 2015/0017227 A1 | * | 1/2015 | Kim | A61K 31/222 424/450 |

FOREIGN PATENT DOCUMENTS

| | | |
|---|---|---|
| EP | 1031348 A2 | 2/2000 |
| EP | 1136062 A1 | 1/2001 |
| JP | 2003081844 A | 3/2003 |
| JP | 2003238394 A | 8/2003 |
| JP | 2004107225 A | 4/2004 |
| KR | 10-0804517 B1 | 2/2008 |
| KR | 10-2013-0075191 A | 7/2013 |
| KR | 10-2014-0096770 A | 8/2014 |
| KR | 10-2015-0008009 A | 1/2015 |
| KR | 1020150129135 A | 11/2015 |
| KR | 1020170042252 A | 7/2016 |
| WO | 03022257 A1 | 3/2003 |

OTHER PUBLICATIONS

Brain et al., Drugs and the pharmaceutical sciences, 2008, 177:651-664.*
Kusuki et al. JP10087409, 1998 (English translated version).*
Pennino et al., Journal of Immunology, 2010, 184(9): 4880-4888.*
Pietrzak et al., Folia Histochemica et Cytobiologica, 2008, 46(1): 11-21.*
Mu Hyun Jin, M.S. et al., Cedrol Enhances Extracellular Matrix Production in Dermal Fibroblasts in a MAPK-Dependent Manner, Ann Dermatol. Feb. 2012, vol. 24, No. 1, p. 16-21, http://dx.doi.org/10.5021/ad.2012.24.1.16.
The extended European search report, 18165746.1, dated Jul. 20, 2018.
Zhang et al., "Hair growth promoting activity of cedrol isolated from the leaves of Platycladus orientalis", Biomedicine & Pharmacotherapy, 2016, vol. 83, pp. 641-647.
Ryu et al., "Anti-aging Effects of Cedrol and Collagen-derived Peptide", J. Soc. Cosmet. Sci. Korea, 2015, vol. 41, No. 3, pp. 229-235.

\* cited by examiner

*Primary Examiner* — Rei Tsang Shiao
(74) *Attorney, Agent, or Firm* — Lucas & Mercanti, LLP

(57) ABSTRACT

The present invention relates to a pharmaceutical composition for preventing or treating autoimmune diseases having cedrol or a pharmaceutically acceptable salt thereof as an active ingredient. Particularly, the cedrol or the derivative thereof of the present invention inhibits the expression of IL-17A, and in particular, cedrol, cedryl acetate, and cedrene exhibit the effect of delaying the outbreak of psoriasis and treating thereof in a psoriasis animal model. Therefore, these compounds can be used for the treatment of autoimmune diseases mediated by IL-17.

2 Claims, 27 Drawing Sheets

IMQ D6    C D6    CA D6    CE D6

IMQ D7    C D7    CA D7    CE D7

IMQ D10   C D10   CA D10   CE D10

IMQ D11   C D11   CA D11   CE D11

IMQ D12     C D12     CA D12     CE D12

IMQ D13     C D13     CA D13     CE D13

COSMETIC COMPOSITION FOR PREVENTING OR AMELIORATING HYPERSENSITIVE SKIN COMPRISING CEDROL OR DERIVATIVES THEREOF, OR PHARMACEUTICALLY ACCEPTABLE SALTS THEREOF

CROSS-REFERENCE TO RELATED APPLICATIONS

This patent application claims priority of Korean Patent Application No. 10-2017-0044176, filed Apr. 5, 2017 and Korean Patent Application No. 10-2017-0076435, filed Jun. 16, 2017, the entire contents of each of which are incorporated herein by reference.

FIELD OF THE INVENTION

The present invention relates to a pharmaceutical composition for preventing or treating autoimmune diseases comprising cedrol or a derivative thereof, or a pharmaceutically acceptable salt thereof as an active ingredient.

DESCRIPTION OF THE RELATED ART

Immunity is one of the self-protection systems to protect a living body from all the foreign substances that enter or are injected into the living tissue. All normal individuals do not react negatively against the self-forming antigens, whereas they have the ability to recognize and respond to the non-self antigens and are capable of eliminating them. However, if a host fails to distinguish the self-antigen from the foreign antigen and thereby induces an abnormal immune response, endogenous immune cells attack the cellular components of the body to cause various diseases, which is called autoimmune disease.

Autoimmune disease is caused by various reasons including heredity, stress, hormone, heavy metal, food, infection, and pesticide, etc. The outbreak rate of this disease is about 5 to 8% globally. Autoimmune disease can also be caused by the excess of IL-17 cytokine. Once antigen-presenting cells (APC) recognize an antigen in the body, various T cells are activated depending on the kind of cytokine secreted by the cells. In particular, when Th17 cells are activated, cytokines such as interleukin-17A (IL-17A), interleukin-17F (IL-17F), interleukin-21 (IL-21), or interleukin-22 (IL-22), activate the immune system. Among the cytokines above, when IL-17A and IL-17F are over-expressed, they form a homodimer or a heterodimer, which binds to the interleukin-17 receptor A (IL-17RA) and interleukin-17 receptor C (IL-17RC) expressed on the skin or mucosal cells to cause inflammation and cell destruction. When the secreted IL-17 acts on vascular endothelial cells, thrombosis or inflammation occurs. When the secreted IL-17 acts on epithelial tissues, various inflammation reactions occur on the skin or mucosa. In addition, when the secreted IL-17 acts on macrophages or dendritic cells, it causes not only various inflammations but also cartilage tissue damage. When the secreted IL-17 acts on osteoblasts, osteoporosis is induced. Therefore, in order to suppress various autoimmune diseases, a compound capable of inhibiting the activation of Th17 cells secreting IL-17 or a compound capable of blocking the expression of IL-17 needs to be developed for the treatment or prevention of the autoimmune disease mediated by IL-17.

The over-secretion of IL-17 in various organs or tissues results in various diseases. For example, the over-secretion of IL-17 in the mucous membranes of the digestive or respiratory tracts causes Crohn's disease, inflammatory bowel disease, type 1 diabetes, and asthma. The over-secretion of IL-17 in the osteoarticulation system causes osteoarthritis, rheumatoid arthritis, polymyalgia rheumatica, ankylosing spondylitis, and psoriatic arthritis. The over-secretion of IL-17 in the nervous system causes multiple sclerosis, IL-17-induced dementia, peripheral neuropathy, and autism. The over-secretion of IL-17 in the vascular system causes uveitis, dry eye disease, and allograft rejection. In addition, when chronic inflammation is induced by the over-secretion of IL-17 in a specific organ, it can trigger the development of such cancers as gastric cancer, pancreatic cancer, breast tumor, ovarian cancer, colorectal cancer, and lung cancer. Therefore, such disease can be prevented or treated by the suppression of the IL-17 secretion.

Currently, anti-inflammatory and immuno-suppressive drugs are used for the treatment of autoimmune diseases. However, some patients show resistance against those drugs, which makes the treatment difficult.

Psoriasis, one of the autoimmune diseases, is a noncommunicable chronic skin disease which repeats worsening and improvement. When psoriasis is first developed, a millet-like red rash is observed on the skin and then it grows as being layered with white skin keratinocytes. Psoriasis can be developed in all ages, but is most common in twenties, followed by teenagers and thirties. Psoriasis has a worldwide prevalence of about 3% and is steadily increasing. Recently, it has been known that the pathogenesis of psoriasis is through IL-23/Th17/IL-17 pathway. Since there are not many drugs that inhibit IL-17, such steroid agents as methotrexate and etretinate are clinically used as therapeutic agents for psoriasis, but such steroid agents have side effects such as liver damage and fetal malformation.

Therefore, studies have been undergoing to develop a therapeutic agent for autoimmune disease without side effects. Particularly, Korean Patent Publication No. 10-2014-0096770 describes a composition for treating autoimmune disease or inflammatory disease comprising Martensia bibarihi extract as an active ingredient. And Korean Patent No. 10-0804517 describes a therapeutic agent for autoimmune disease comprising *Sophora flavescens* extract.

In the course of a study to develop a therapeutic agent for autoimmune disease without in vivo side effects, the present inventors found that cedrol, cedryl acetate, alpha-cedrene, methyl cedryl ketone, methyl cedryl ether, and cedrene epoxide inhibit the expression of IL-17. In particular, the present inventors confirmed that cedrol, cedryl acetate, and alpha-cedrene were effective in delaying the development of psoriasis and treating psoriasis in a psoriasis animal model, leading to the completion of this present invention providing a composition for preventing and treating autoimmune diseases.

SUMMARY OF THE INVENTION

It is an object of the present invention to provide a pharmaceutical composition for preventing or treating autoimmune diseases, a health functional food for improving autoimmune diseases, or a cosmetic composition for alleviating skin irritation comprising one or more compounds selected from the group consisting of the compounds represented by formulas 1~6 or a pharmaceutically acceptable salt thereof as an active ingredient:

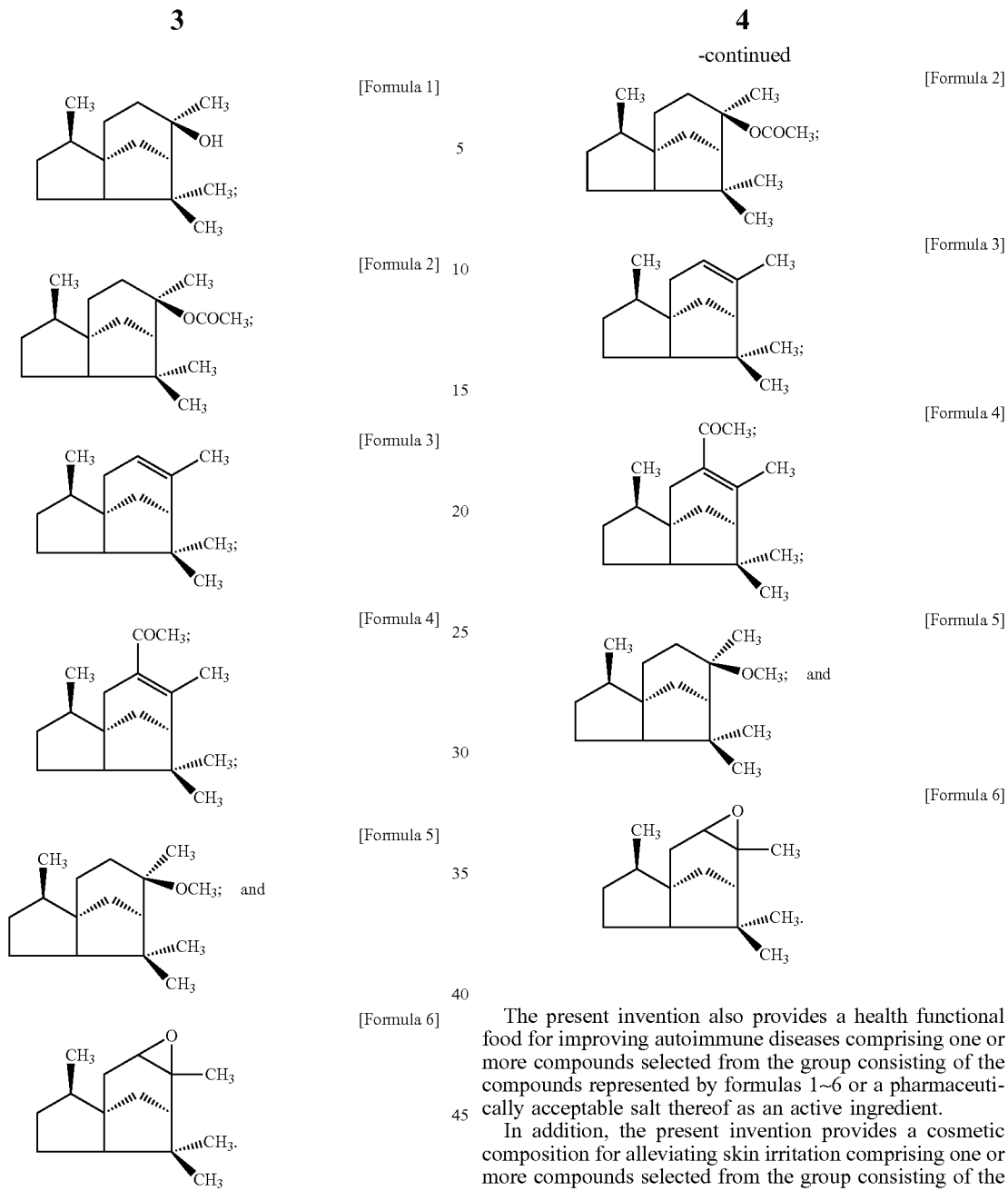

To achieve the above object, the present invention provides a pharmaceutical composition for preventing or treating autoimmune diseases comprising one or more compounds selected from the group consisting of the compounds represented by formulas 1~6 or a pharmaceutically acceptable salt thereof as an active ingredient:

The present invention also provides a health functional food for improving autoimmune diseases comprising one or more compounds selected from the group consisting of the compounds represented by formulas 1~6 or a pharmaceutically acceptable salt thereof as an active ingredient.

In addition, the present invention provides a cosmetic composition for alleviating skin irritation comprising one or more compounds selected from the group consisting of the compounds represented by formulas 1~6 or a pharmaceutically acceptable salt thereof as an active ingredient.

The cedrol or its derivatives of the present invention can inhibit the expression of IL-17A. In particular, cedrol, cedryl acetate, and alpha-cedrene were confirmed to be effective in delaying the development of psoriasis and in treating the disease in a psoriasis animal model, indicating the said compounds could be effectively used for the treatment of autoimmune diseases mediated by IL-17.

BRIEF DESCRIPTION OF THE DRAWINGS

The application of the preferred embodiments of the present invention is best understood with reference to the accompanying drawings, wherein.

DETAILED DESCRIPTION OF THE INVENTION

Figure 1:
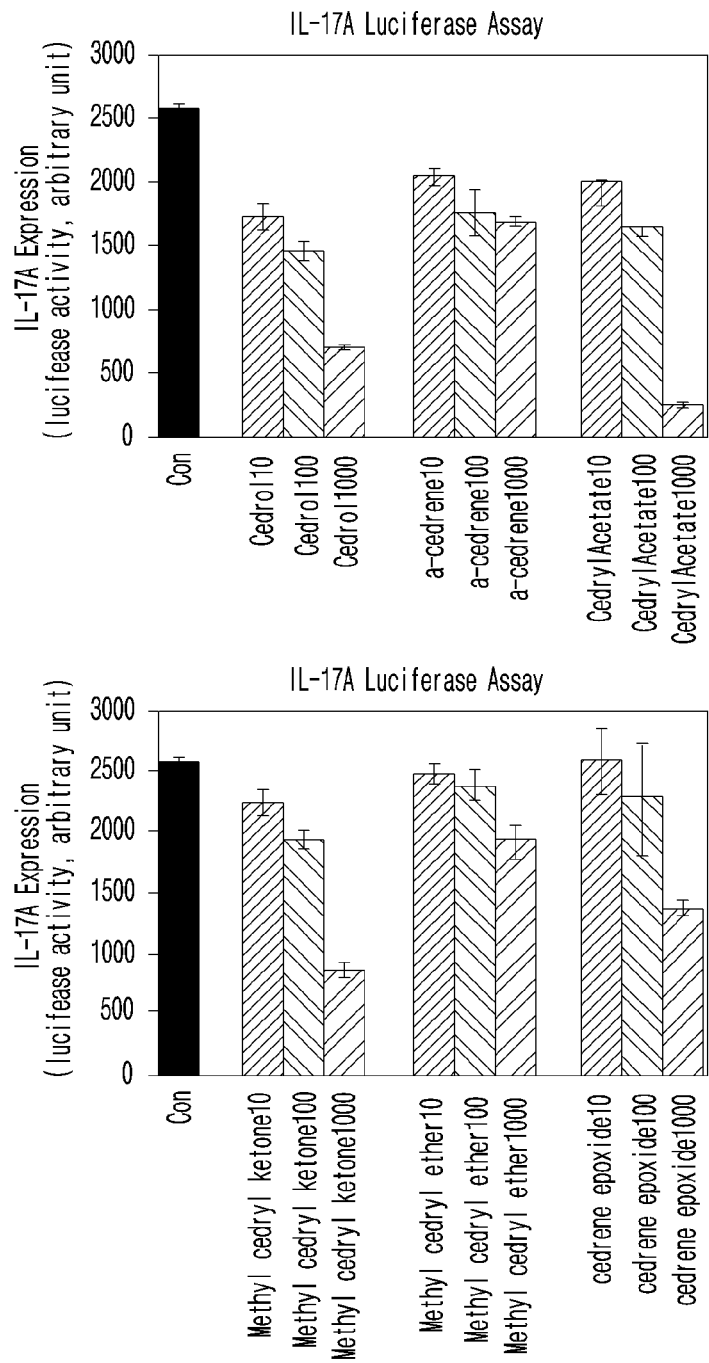
FIG. 1 is a graph illustrating the inhibitory effect of cedrol, cedryl acetate, alpha-cedrene, methyl cedryl ketone, methyl cedryl ether, and cedrene epoxide on the expression of IL-17A (Con: the control group not-treated with any of those compounds).
Figure 2A:
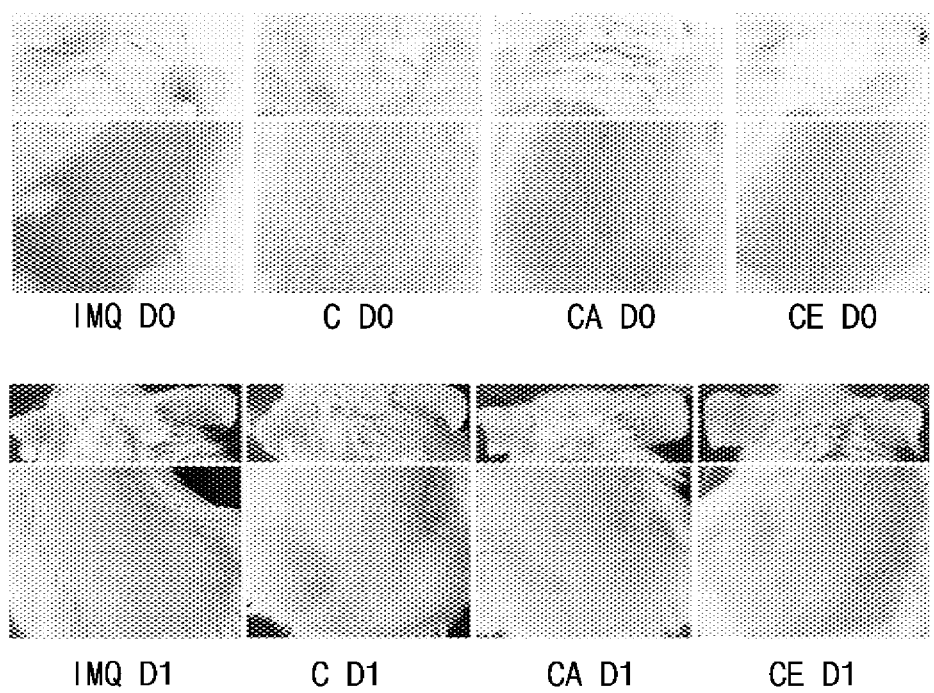
FIG. 2A is a set of photographs illustrating the therapeutic effect of distilled water (IMQ), cedrol (C), cedryl acetate (CA), or alpha-cedrene (CE) on psoriasis induced by imiquimod in the ear and the back of a mouse, observed before (D0) or one day after (D1) the application of imiquimod while the compound was orally administered to the mouse.
Figure 2B:
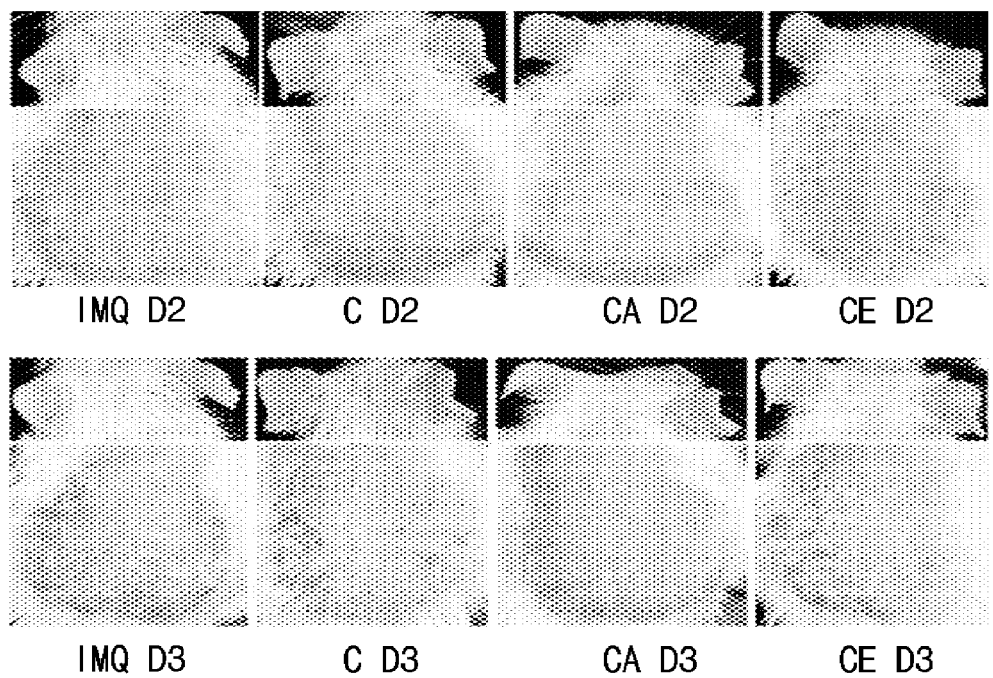
FIG. 2B is a set of photographs illustrating the therapeutic effect of distilled water (IMQ), cedrol (C), cedryl acetate (CA), or alpha-cedrene (CE) on psoriasis induced by imiquimod in the ear and the back of a mouse, observed two days after (D2) or three days after (D3) the application of imiquimod while the compound was orally administered to the mouse.
Figure 2C:
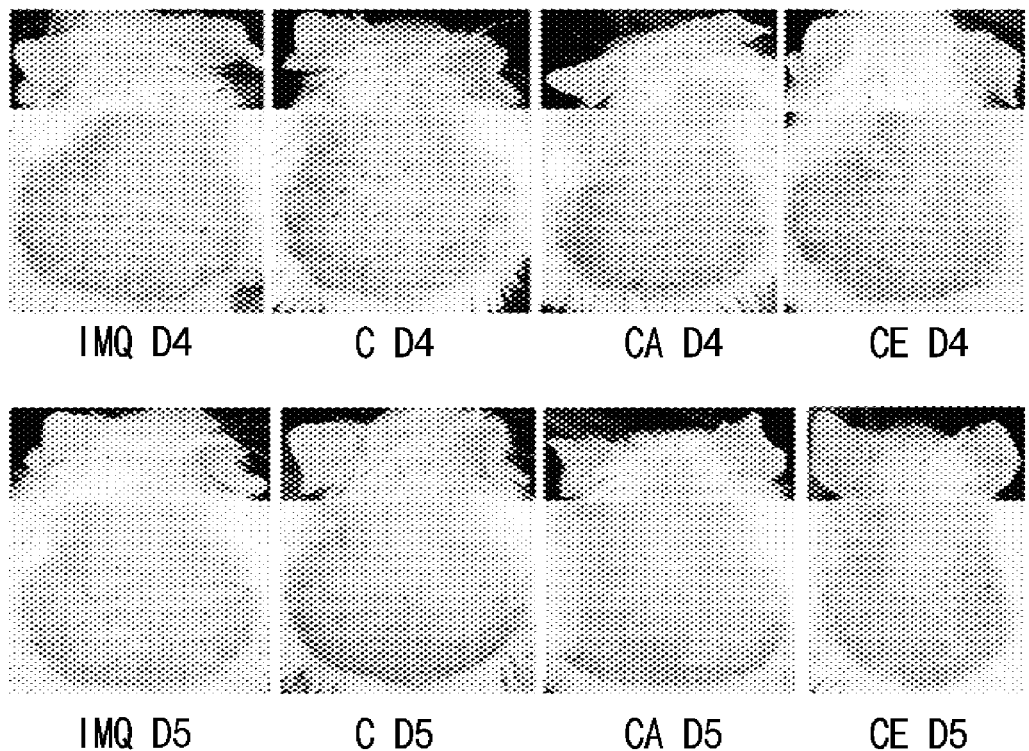
FIG. 2C is a set of photographs illustrating the therapeutic effect of distilled water (IMQ), cedrol (C), cedryl acetate (CA), or alpha-cedrene (CE) on psoriasis induced by imiquimod in the ear and the back of a mouse, observed four days after (D4) or five days after (D5) the application of imiquimod while the compound was orally administered to the mouse.
Figure 2D:
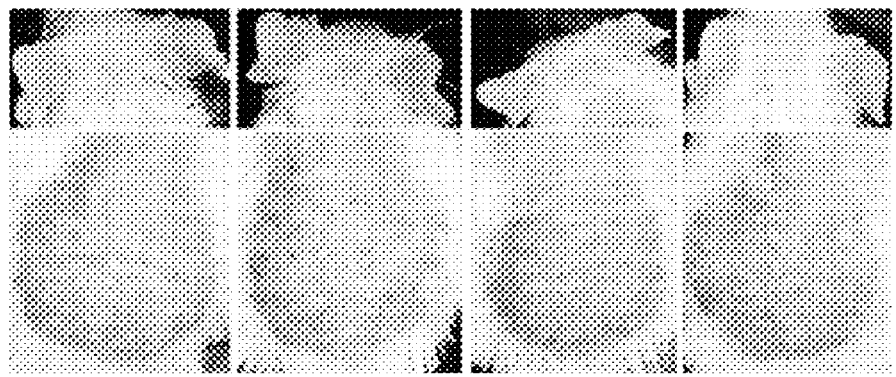
FIG. 2D is a set of photographs illustrating the therapeutic effect of distilled water (IMQ), cedrol (C), cedryl acetate (CA), or alpha-cedrene (CE) on psoriasis induced by imiquimod in the ear and the back of a mouse, observed six days after (D6) or seven days after (D7) the application of imiquimod while the compound was orally administered to the mouse.
Figure 2D:
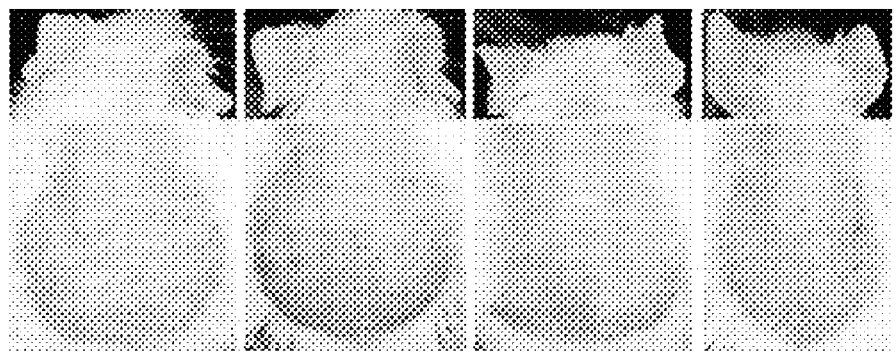

Hereinafter, the present invention is described in detail.

The present invention provides a pharmaceutical composition for preventing or treating autoimmune diseases comprising one or more compounds selected from the group consisting of the compounds represented by formulas 1~6 or a pharmaceutically acceptable salt thereof as an active ingredient.

TABLE 1

| Formula | Compound | Chemical structure |
| --- | --- | --- |
| 1 | Cedrol | [structure] |
| 2 | Cedryl acetate | [structure] |
| 3 | Alpha-cedrene | [structure] |
| 4 | Methyl cedryl ketone | [structure] |
| 5 | Methyl cedryl ether | [structure] |
| 6 | Cedrene epoxide | [structure] |

The compounds represented by formulas 1~6 of the present invention can be used as the form of a pharmaceutically acceptable salt, in which the salt is preferably acid addition salt formed by pharmaceutically acceptable free acids. The acid addition salt can be obtained from inorganic acids such as hydrochloric acid, nitric acid, phosphoric acid, sulfuric acid, hydrobromic acid, hydroiodic acid, nitrous acid and phosphorous acid, or non-toxic organic acids such as aliphatic mono/dicarboxylate, phenyl-substituted alkanoate, hydroxy alkanoate, alkandioate, aromatic acids and aliphatic/aromatic sulfonic acids. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate and mandelate.

The acid addition salt in this invention can be prepared by the conventional method known to those in the art. For example, the compounds of formulas 1~6 are dissolved in an organic solvent such as methanol, ethanol, acetone, methylenechloride, or acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in the organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The compounds represented by formulas 1~6 above have a non-symmetrical structure, so that they exist in the form of different enantiomers. So, all the compounds represented by formulas 1~6 can include all the optical isomers, (R) or (S) type stereoisomers, or the mixtures thereof. The compound represented by formula 1 can contain the racemic body thereof, one or more enantiomers, one or more diasteromers, or the mixtures thereof. The optical isomer according to the present invention can be obtained by the separation method or the preparation method well known to those in the art.

The autoimmune disease herein can be mediated by interleukin-17. Particularly, the autoimmune disease above can be selected from the group consisting of psoriasis, eczema, scleroderma, vitiligo, Crohn's disease, inflammatory bowel disease, type 1 diabetes, asthma, osteoarthritis, rheumatoid arthritis, polymyalgia rheumatica, ankylosing spondylitis, psoriatic arthritis, multiple sclerosis, IL-17-induced dementia, peripheral neuropathy, autism, uveitis, dry eye disease, allograft rejection, gastric cancer, pancreatic cancer, breast tumor, ovarian cancer, colorectal cancer, and lung cancer.

In a preferred embodiment of the present invention, the present inventors confirmed that the cedrol or the derivatives thereof inhibited the expression of IL-17A using cedrol, cedryl acetate, alpha-cedrene, methyl cedryl ketone, methyl cedryl ether, and cedrene epoxide (see FIG. 1).

Figure 4:
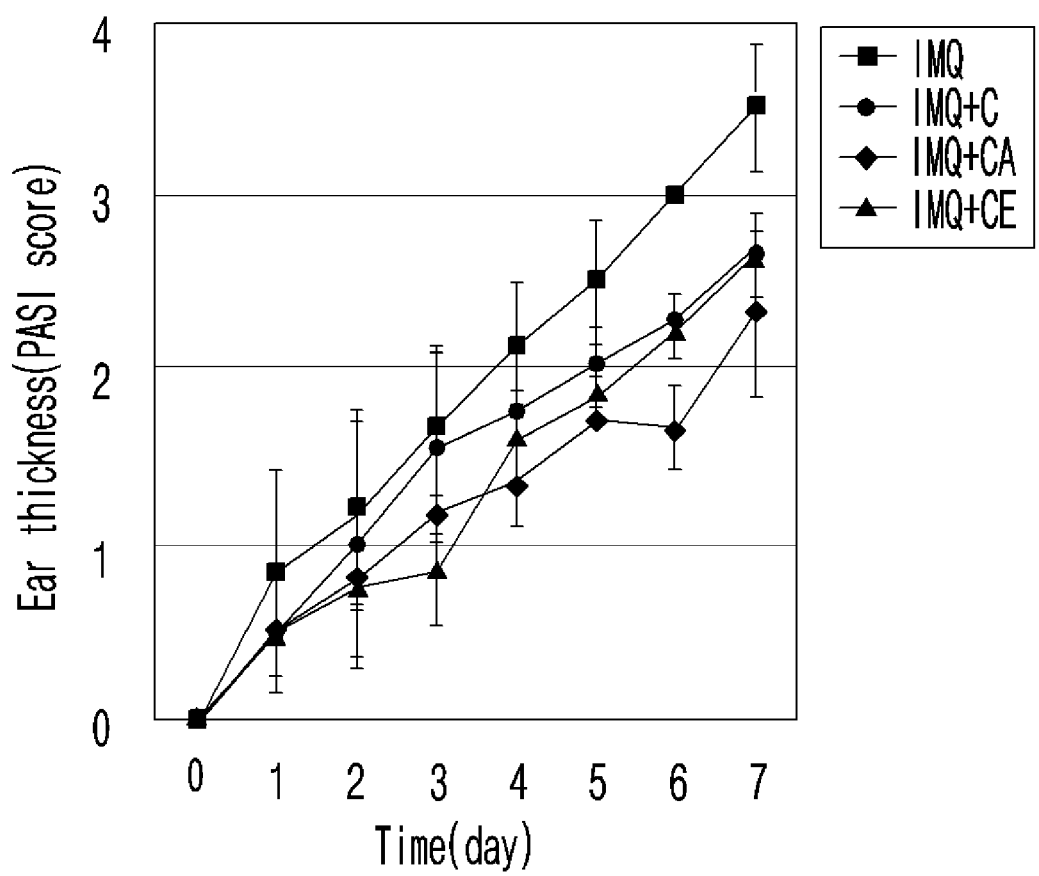
FIG. 4 is a graph illustrating the comparison of the reduction effect on the ear thickness of the psoriasis induced mice according to the oral administration of distilled water (IMQ), cedrol (IMQ+C), cedryl acetate (IMQ+CA), or alpha-cedrene (IMQ+CE) after the application of imiquimod.
Figure 5:
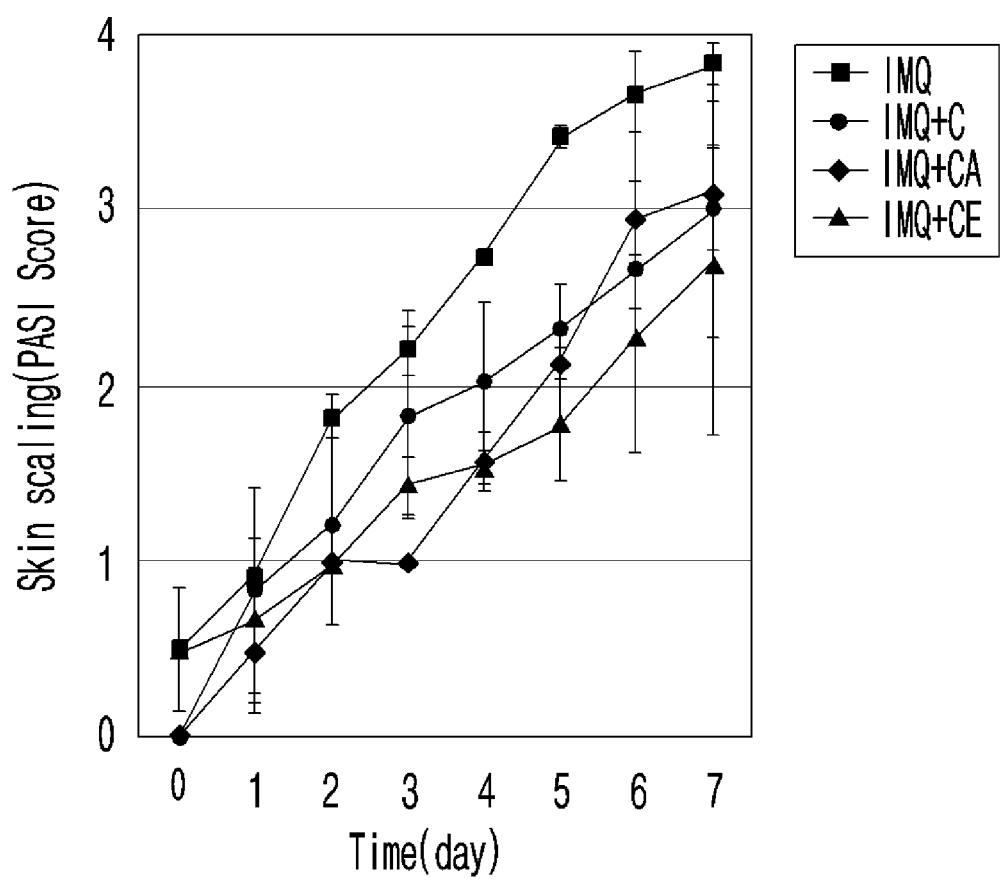
FIG. 5 is a graph illustrating the comparison of the reduction effect on keratosis of the psoriasis induced mice according to the oral administration of distilled water (IMQ), cedrol (IMQ+C), cedryl acetate (IMQ+CA), or alpha-cedrene (IMQ+CE) after the application of imiquimod.
Figure 6:
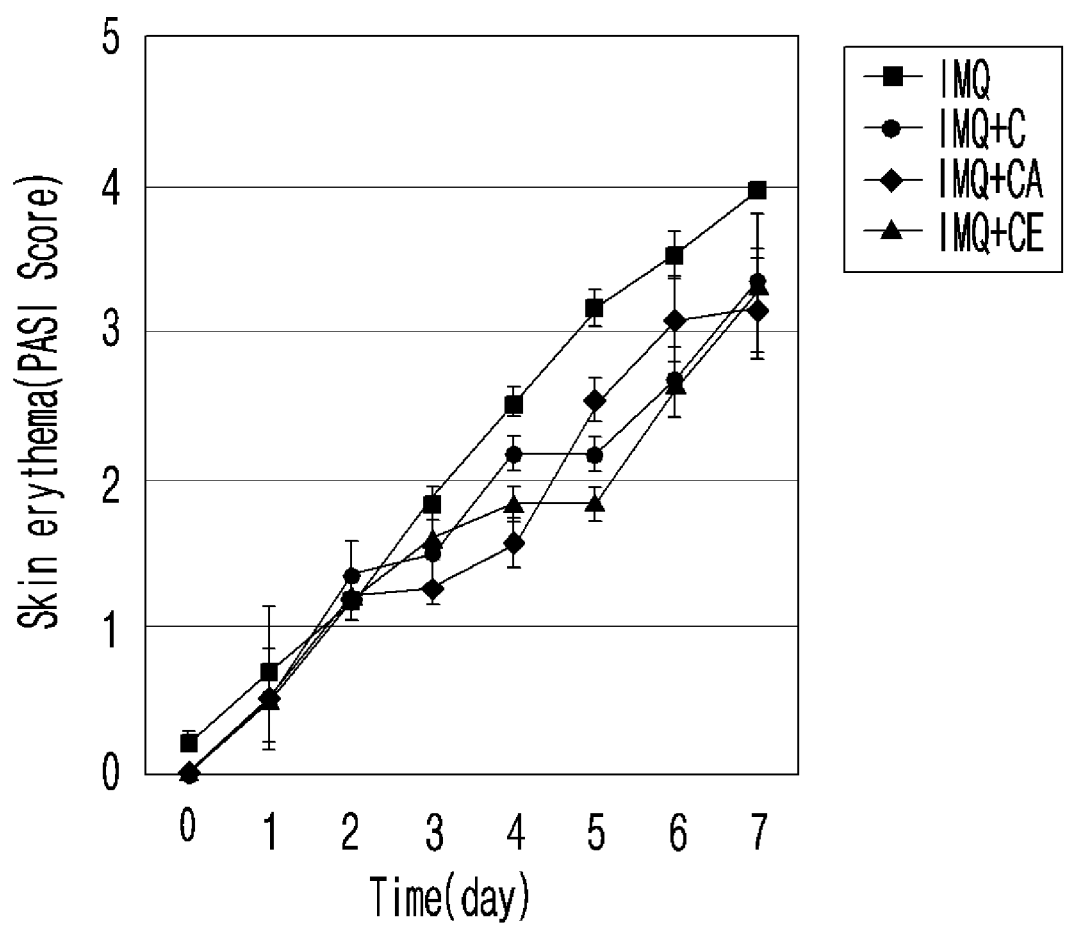
FIG. 6 is a graph illustrating the comparison of the reduction effect on skin flair of the psoriasis induced mice according to the oral administration of distilled water (IMQ), cedrol (IMQ+C), cedryl acetate (IMQ+CA), or alpha-cedrene (IMQ+CE) after the application of imiquimod.
Figure 9:
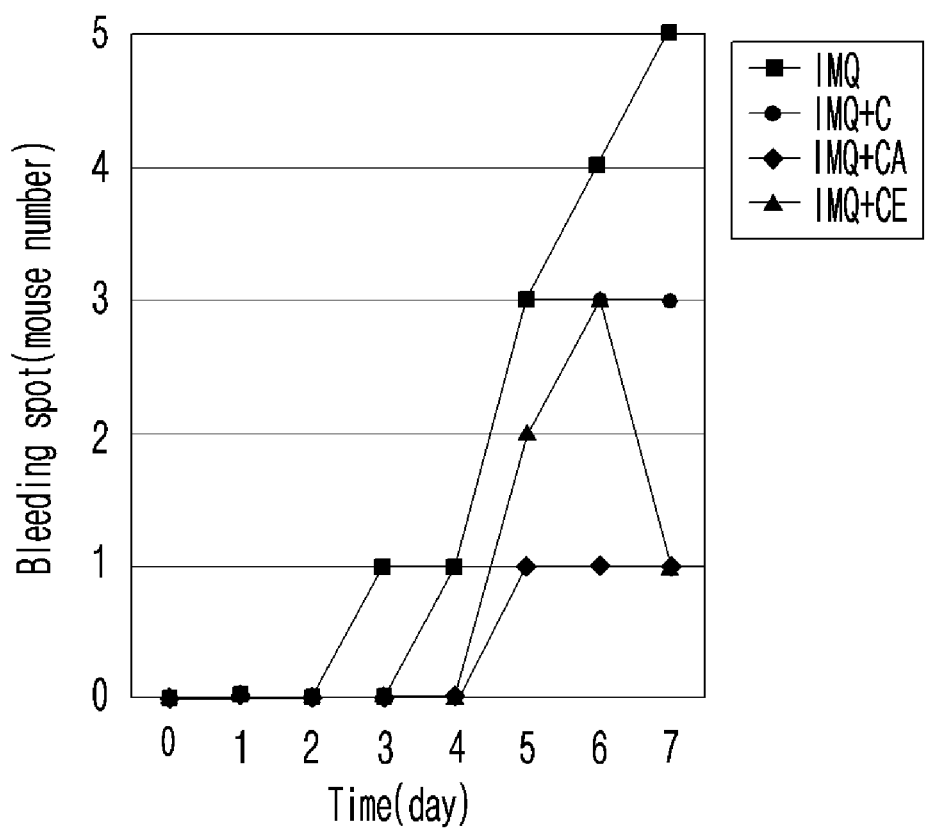
FIG. 9 is a graph illustrating the comparison of the reduction effect on skin hemorrhage spots of the psoriasis induced mice according to the oral administration of distilled water (IMQ), cedrol (IMQ+C), cedryl acetate (IMQ+CA), or alpha-cedrene (IMQ+CE) after the application of imiquimod.
Figure 10:
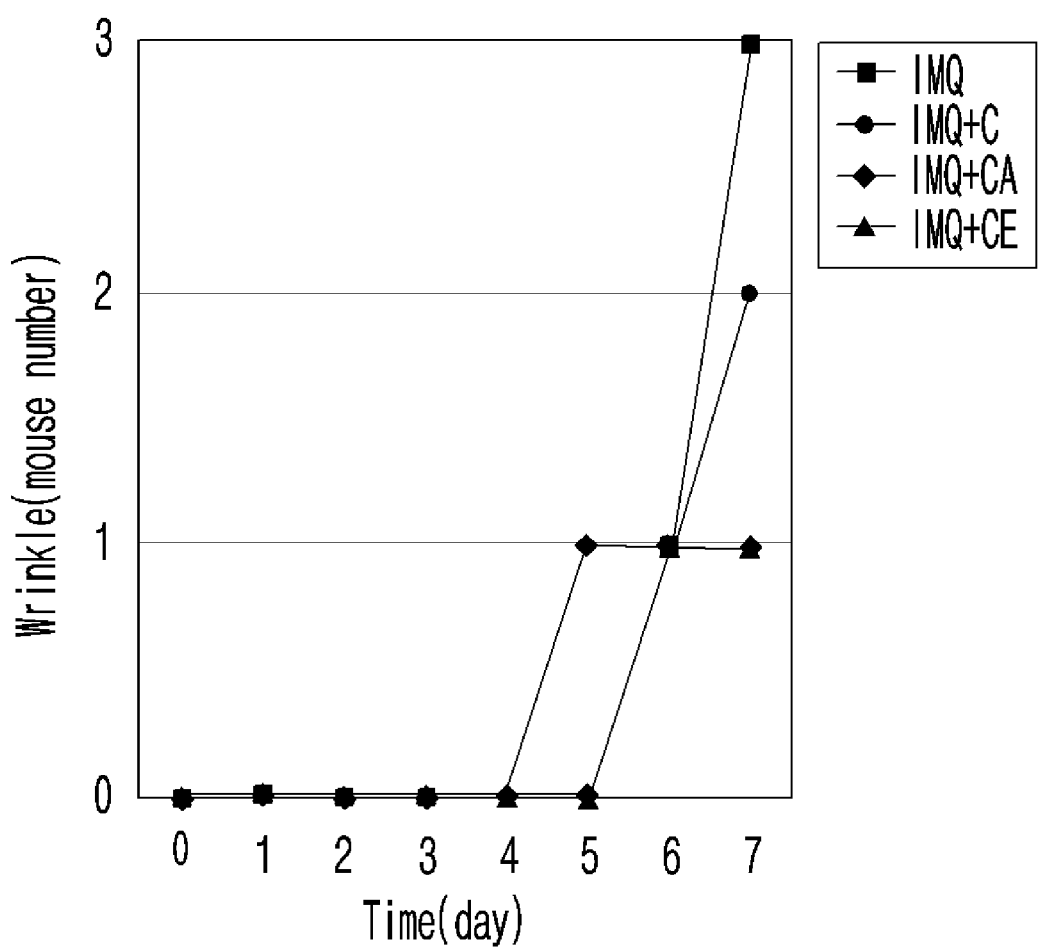
FIG. 10 is a graph illustrating the comparison of the reduction effect on skin wrinkles of the psoriasis induced mice according to the oral administration of distilled water (IMQ), cedrol (IMQ+C), cedryl acetate (IMQ+CA), or alpha-cedrene (IMQ+CE) after the application of imiquimod.

The present inventors observed the ear thickness (see FIG. 4), keratosis (see FIG. 5), skin flair (see FIG. 6), skin pain (see FIG. 8), skin hemorrhage spots (see FIG. 9), and skin wrinkles (see FIG. 10) in the psoriasis induced mice according to the oral administration of cedrol, cedryl acetate, and alpha-cedrene. As a result, the present inventors confirmed that those compounds were effective in reducing the ear thickness, keratosis, skin flair, skin pain, skin hemorrhage spots, and skin wrinkles and also efficient in inhibiting the expression of IL-17A in the spleen (see FIG. 11). It was also confirmed that the thickness of the epidermal layer was thinner than that of the control group (see FIG. 12).

Figure 14:
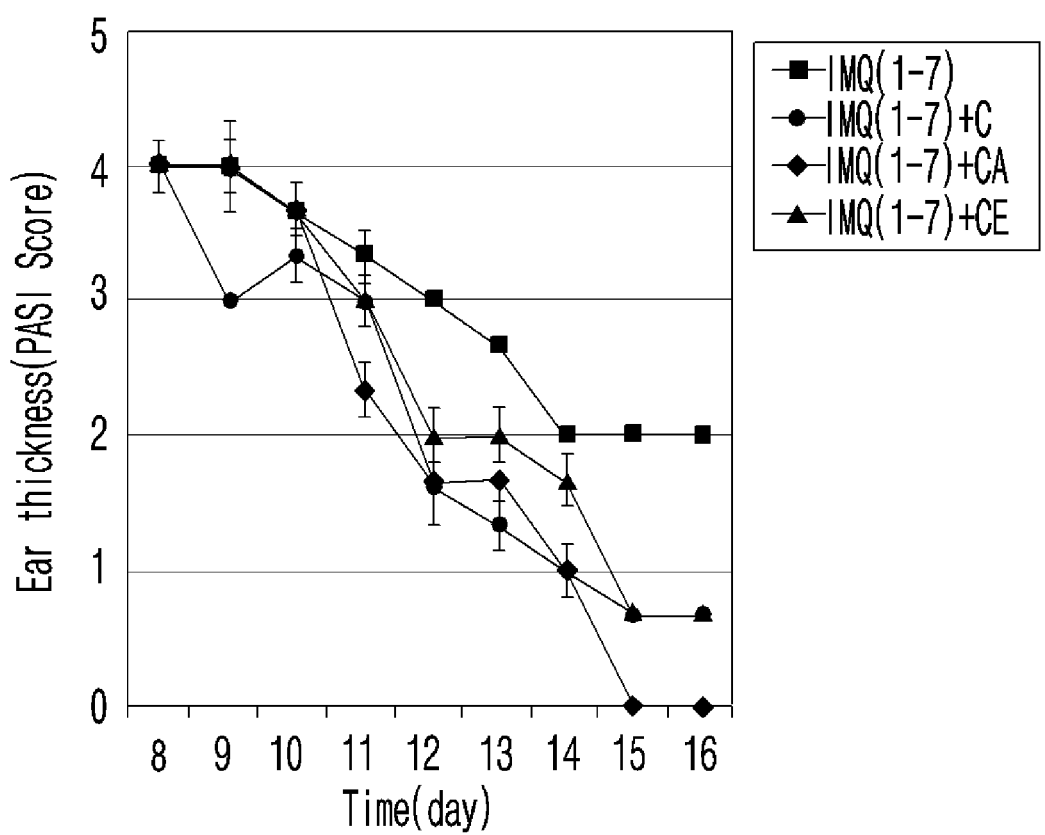
FIG. 14 is a graph illustrating the comparison of the recovery effect on ear thickness of the psoriasis induced mice according to the oral administration of distilled water (IMQ(1-7)), cedrol (IMQ(1-7)+C), cedryl acetate (IMQ(1-7)+CA), or alpha-cedrene (IMQ(1-7)+CE) after the termination of imiquimod application.
Figure 15:
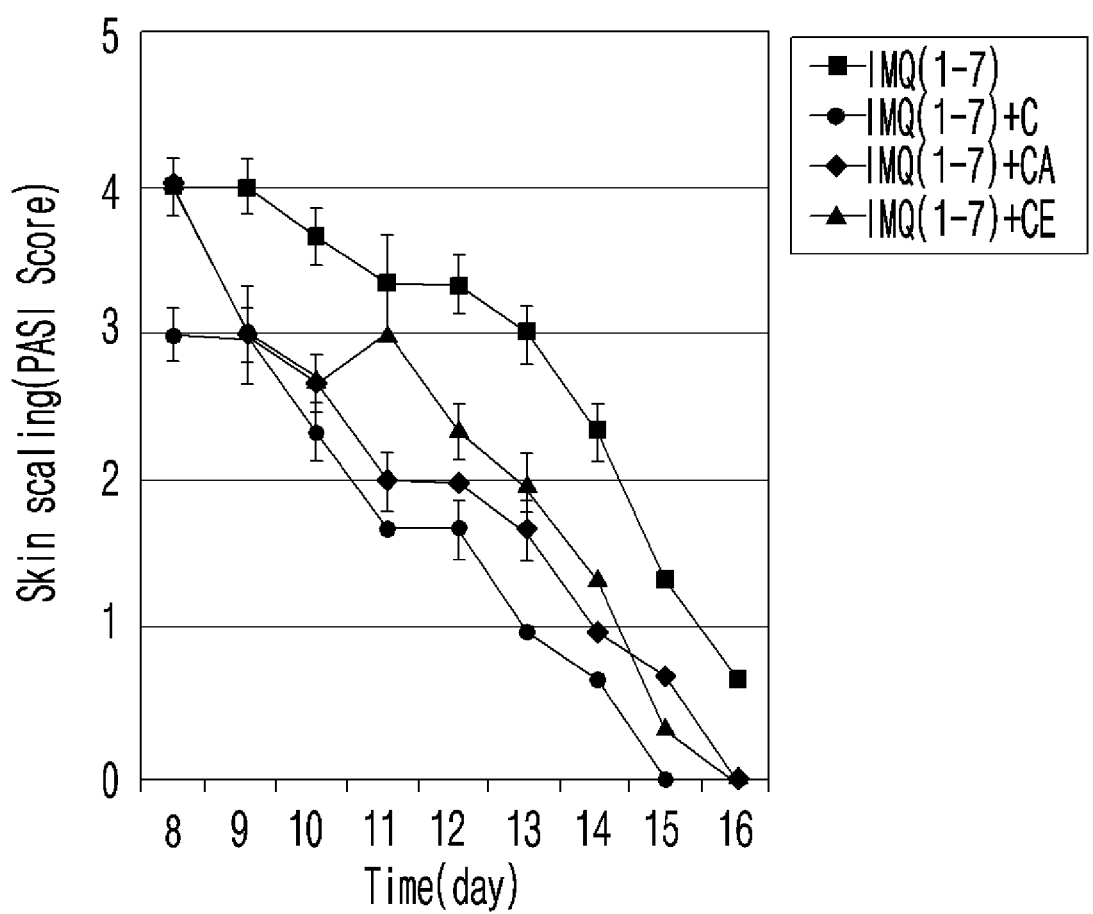
FIG. 15 is a graph illustrating the comparison of the recovery effect on keratosis in the psoriasis induced mice according to the oral administration of distilled water (IMQ (1-7)), cedrol (IMQ(1-7)+C), cedryl acetate (IMQ(1-7)+CA), or alpha-cedrene (IMQ(1-7)+CE) after the termination of imiquimod application.
Figure 16:
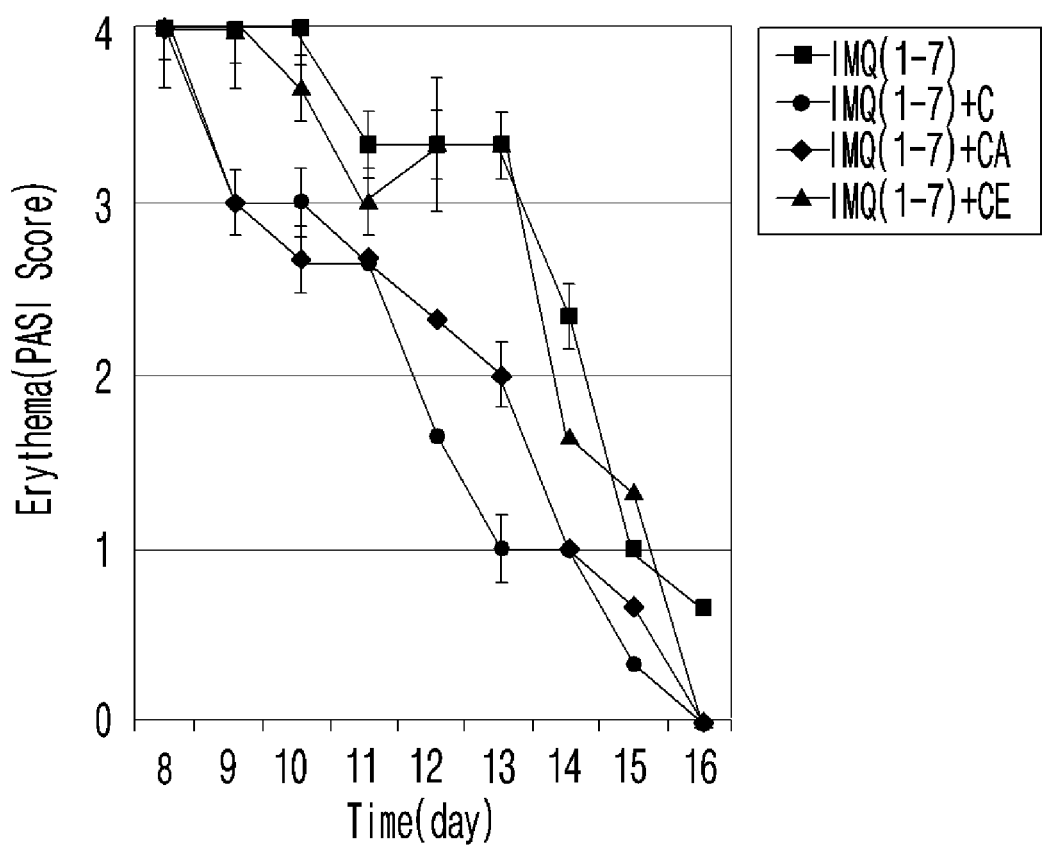
FIG. 16 is a graph illustrating the comparison of the recovery effect on skin flair in the psoriasis induced mice according to the oral administration of distilled water (IMQ(1-7)), cedrol (IMQ(1-7)+C), cedryl acetate (IMQ(1-7)+CA), or alpha-cedrene (IMQ(1-7)+CE) after the termination of imiquimod application.
Figure 18:
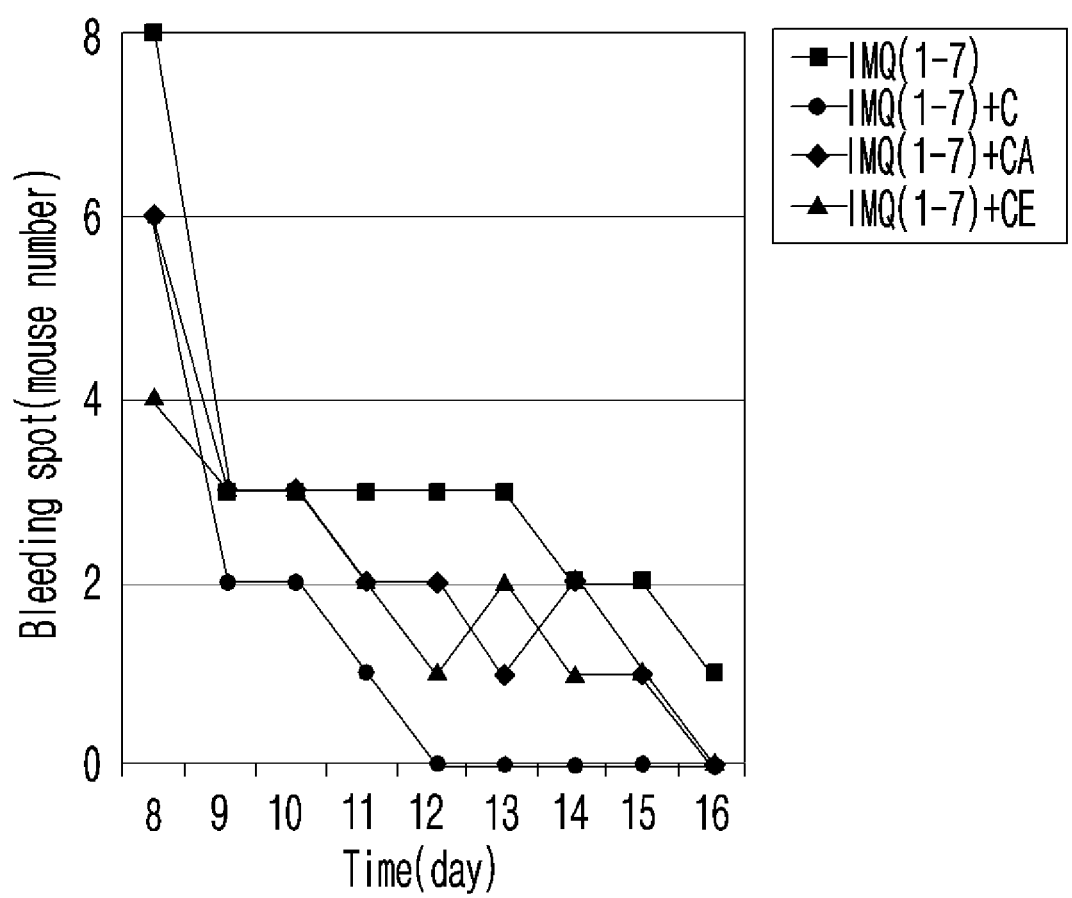
FIG. 18 is a graph illustrating the comparison of the recovery effect on skin hemorrhage spots in the psoriasis induced mice according to the oral administration of distilled water (IMQ(1-7)), cedrol (IMQ(1-7)+C), cedryl acetate (IMQ(1-7)+CA), or alpha-cedrene (IMQ(1-7)+CE) after the termination of imiquimod application.
Figure 19:
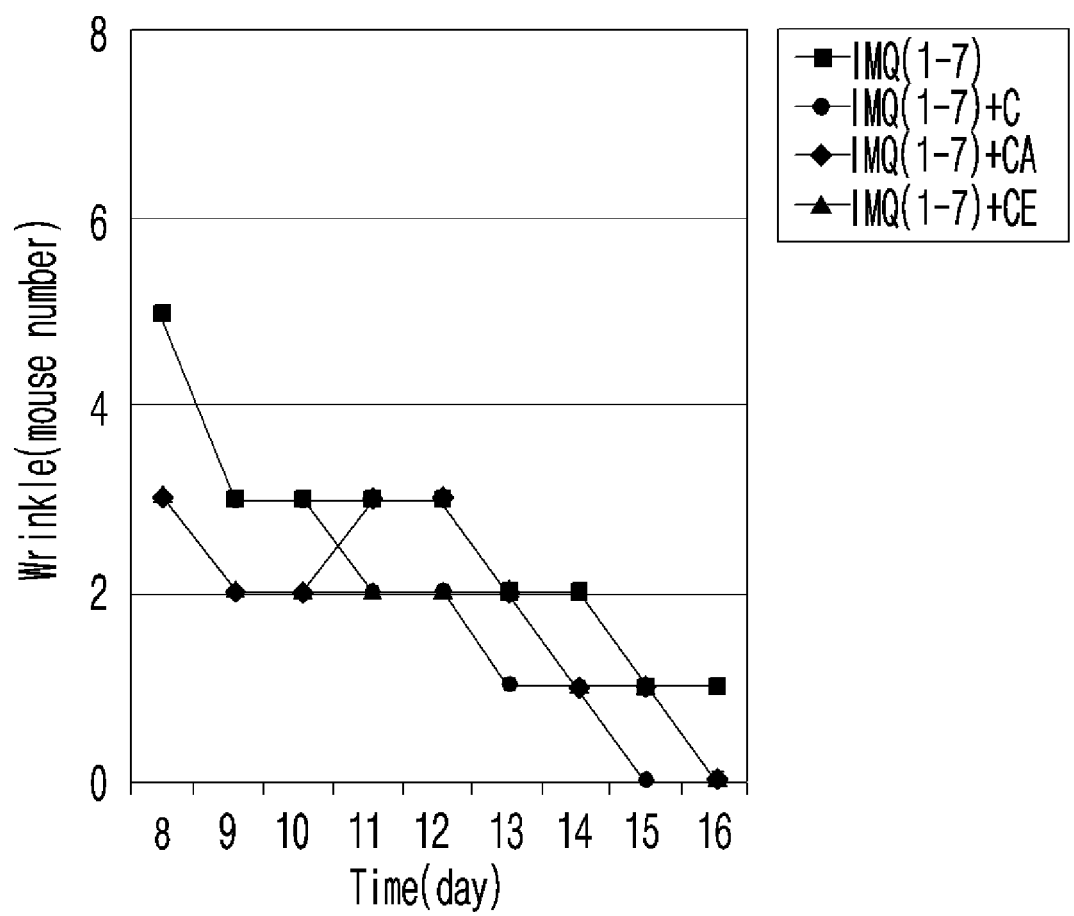
FIG. 19 is a graph illustrating the comparison of the recovery effect on skin wrinkles in the psoriasis induced mice according to the oral administration of distilled water (IMQ(1-7)), cedrol (IMQ(1-7)+C), cedryl acetate (IMQ(1-7)+CA), or alpha-cedrene (IMQ(1-7)+CE) after the termination of imiquimod application.
Figure 20:
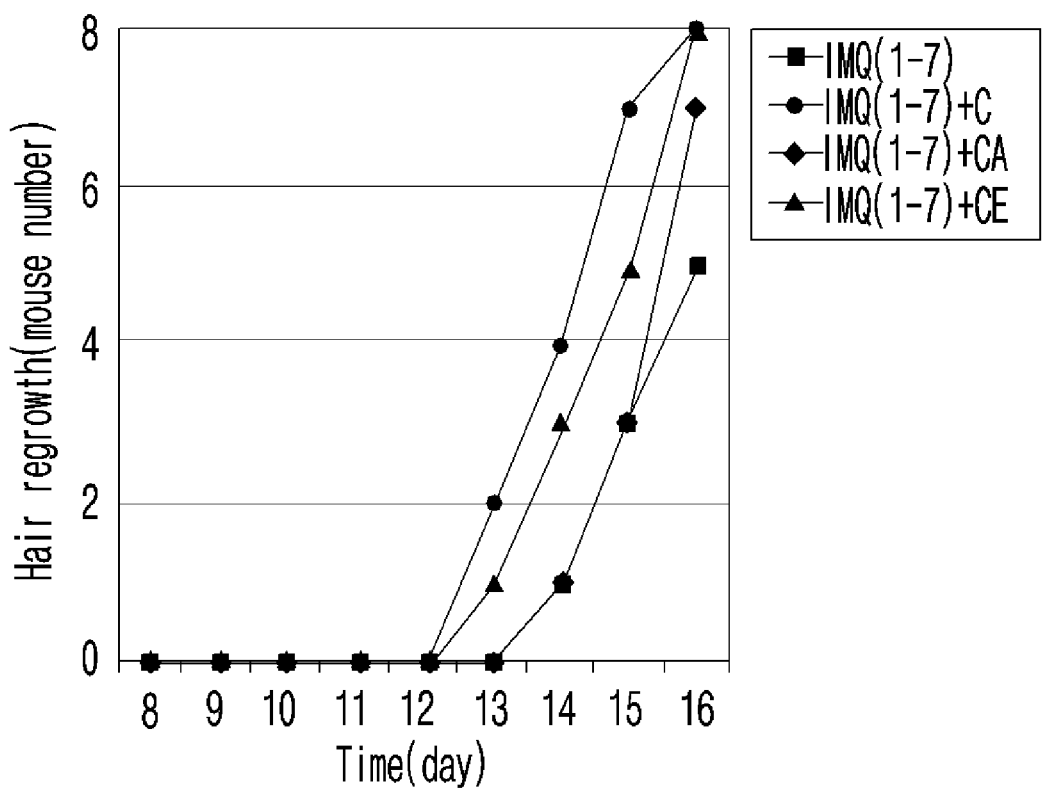
FIG. 20 is a graph illustrating the comparison of the accelerating effect on hair regrowth in the psoriasis induced mice according to the oral administration of distilled water (IMQ(1-7)), cedrol (IMQ(1-7)+C), cedryl acetate (IMQ(1-7)+CA), or alpha-cedrene (IMQ(1-7)+CE) after the termination of imiquimod application.

In addition, the present inventors confirmed that the oral administration of cedrol, cedryl acetate, and alpha-cedrene to the psoriasis induced mice was efficient not only in the recovery of the ear thickness (see FIG. 14), keratosis (see FIG. 15), skin flair (see FIG. 16), skin hemorrhage spots (see FIG. 18), and skin wrinkles (see FIG. 19) but also in accelerating hair regrowth (see FIG. 20).

Therefore, the compounds represented by formulas 1~6 of the present invention can be effectively used for the treatment of autoimmune diseases since they inhibit the expression of IL-17A, and have the effect of delaying the outbreak of psoriasis, the disease mediated by IL-17A, and treating thereof.

The pharmaceutical composition can include the compounds represented by formulas 1~6 or the pharmaceutically acceptable salt thereof by 10 to 95 weight % by the total weight of the composition. The pharmaceutical composition of the present invention can additionally contain one or more active ingredients having the same or similar functions to the compounds.

The pharmaceutical composition of the present invention can include any generally used carrier, diluent, excipient, or a combination of at least two of those. The pharmaceutically acceptable carrier can be any carrier that is able to deliver the composition of the present invention in a living body without limitation, which is exemplified by saline, sterilized water, Ringer's solution, buffered saline, dextrose solution, maltodextrin solution, glycerol, ethanol, liposome and a mixture comprising one or more of those components. If necessary, a general additive such as antioxidant, buffer, and bacteriostatic agent can be additionally added.

The composition of the present invention can be prepared by mixing with generally used diluents or excipients such as fillers, extenders, binders, wetting agents, disintegrating agents and surfactant.

The composition of the present invention can be prepared for oral or parenteral administration. Solid formulations for oral administration are tablets, pills, powders, granules, capsules, and troches. These solid formulations are prepared by mixing with one or more suitable excipients such as starch, calcium carbonate, sucrose or lactose, gelatin, etc. Except for the simple excipients, lubricants, for example magnesium stearate, talc, etc, can be added. Liquid formulations for oral administrations are suspensions, solutions, emulsions and syrups, and the above-mentioned formulations can contain various excipients such as wetting agents, sweeteners, aromatics and preservatives.

Formulations for parenteral administration can include injections such as sterilized aqueous solutions, water-insoluble excipients, suspensions, and emulsions.

Water-insoluble excipients and suspensions can contain propylene glycol, polyethylene glycol, vegetable oil like olive oil, injectable ester like ethylolate, etc.

The composition of the present invention can be administered orally or parenterally according to the desired method. The parenteral administration can be selected from the group consisting of external administration, intraperitoneal injection, intra-rectal injection, subcutaneous injection, intravenous injection, intramuscular injection or intra-thoracic injection.

The composition of the present invention is administered in a pharmaceutically effective dose. The effective dose can be determined according to the type and the severity of a disease, drug activity, drug sensitivity, administration time, administration pathway, excretion rate, treatment period, and other medicines applied together.

The composition of the present invention can be administered alone or in combination with other therapeutic agents. When coadministered, the administration can be performed sequentially or simultaneously.

For a desired effect, the effective dose of the active ingredient contained in the pharmaceutical composition of the present invention can be 0.001 to 10,000 mg/kg, particularly 0.1 to 5 g/kg. The administration frequency can be once a day or a few times a day.

The present invention also provides a health functional food for improving autoimmune diseases comprising one or more compounds selected from the group consisting of the compounds represented by formulas 1~6 or a pharmaceutically acceptable salt thereof as an active ingredient.

According to an example of the present invention, the compound above can be cedrol represented by formula 1, cedryl acetate represented by formula 2, alpha-cedrene represented by formula 3, methyl cedryl ketone represented by formula 4, methyl cedryl ether represented by formula 5, or cedrene epoxide represented by formula 6.

The said compound can have the characteristics described hereinbefore. The autoimmune disease herein can be mediated by interleukin-17. Particularly, the autoimmune disease above can be selected from the group consisting of psoriasis, eczema, scleroderma, vitiligo, Crohn's disease, inflammatory bowel disease, type 1 diabetes, asthma, osteoarthritis, rheumatoid arthritis, polymyalgia rheumatica, ankylosing spondylitis, psoriatic arthritis, multiple sclerosis, IL-17-induced dementia, peripheral neuropathy, autism, uveitis, dry eye disease, allograft rejection, gastric cancer, pancreatic cancer, breast tumor, ovarian cancer, colorectal cancer, and lung cancer.

In a preferred embodiment of the present invention, the present inventors confirmed that cedrol, cedryl acetate, alpha-cedrene, methyl cedryl ketone, methyl cedryl ether, and cedrene epoxide could suppress the expression of IL-17A (see FIG. 1) and in particular cedrol, cedryl acetate, and alpha-cedrene could delay the development of psoriasis (see FIGS. 2a~12) and further treat the disease (see FIGS. 13a~19) in the psoriasis induced animal model.

Therefore, the compounds represented by formulas 1~6 can be effectively used for the improvement of autoimmune diseases mediated by IL-17A.

The compounds represented by formulas 1~6 of the present invention or a pharmaceutically acceptable salt thereof can be used as a food additive. In that case, the compounds represented by formulas 1~6 of the present invention or a pharmaceutically acceptable salt thereof can be added as it is or as mixed with other food components according to the conventional method. The mixing ratio of active ingredients can be regulated according to the purpose of use. In general, to produce a health functional food, the compounds represented by formulas 1~6 of the present invention or a pharmaceutically acceptable salt thereof is added preferably by 0.01~90 weight part to the total food weight.

The form and kind of the health functional food is not limited. The health functional food can be tablets, capsules, powders, granules, liquids, and pills.

The health functional food of the present invention can additionally include various flavors or natural carbohydrates, etc, like other health foods. The natural carbohydrates above can be one of monosaccharides such as glucose and fructose, disaccharides such as maltose and sucrose, polysaccharides such as dextrin and cyclodextrin, and glucose alcohols such as xilytole, sorbitol and erythritol. Besides, natural sweetening agents such as thaumatin and stevia extract, and synthetic sweetening agents such as saccharin and aspartame can be included as a sweetening agent.

In addition to the ingredients mentioned above, the health functional food of the present invention can include in variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, etc. All the mentioned ingredients can be added singly or together. The mixing ratio of those ingredients does not matter in fact, but in general, each can be added by 001~0.1 weight part per 100 weight part of the composition of the present invention.

The present invention also provides a cosmetic composition for alleviating skin irritation comprising one or more compounds selected from the group consisting of the compounds represented by formulas 1~6 or a pharmaceutically acceptable salt thereof as an active ingredient.

According to an example of the present invention, the compound above can be cedrol represented by formula 1, cedryl acetate represented by formula 2, alpha-cedrene represented by formula 3, methyl cedryl ketone represented by formula 4, methyl cedryl ether represented by formula 5, or cedrene epoxide represented by formula 6.

The said compound can have the characteristics described hereinbefore. The autoimmune disease herein can be mediated by interleukin-17. Particularly, the autoimmune disease above can be selected from the group consisting of psoriasis, eczema, scleroderma, vitiligo, Crohn's disease, inflammatory bowel disease, type 1 diabetes, asthma, osteoarthritis, rheumatoid arthritis, polymyalgia rheumatica, ankylosing spondylitis, psoriatic arthritis, multiple sclerosis, IL-17-induced dementia, peripheral neuropathy, autism, uveitis, dry eye disease, allograft rejection, gastric cancer, pancreatic cancer, breast tumor, ovarian cancer, colorectal cancer, and lung cancer.

In a preferred embodiment of the present invention, the present inventors confirmed that cedrol, cedryl acetate, alpha-cedrene, methyl cedryl ketone, methyl cedryl ether, and cedrene epoxide could suppress the expression of IL-17A (see FIG. 1) and in particular cedrol, cedryl acetate, and alpha-cedrene could delay the development of psoriasis (see FIGS. 2a~12) and further treat the disease (see FIGS. 13a~19) in the psoriasis induced animal model.

Therefore, the compounds represented by formulas 1~6 can be effectively used for the alleviation of autoimmune diseases mediated by IL-17A.

The compounds represented by formulas 1~6 of the present invention or a pharmaceutically acceptable salt thereof can be included in the cosmetic composition by 0.1 to 50 weight %, particularly 1 to 10 weight % to the total weight of the cosmetic composition. However, the ratio above can be changed according to the form of cosmetics, the specific application site (face or hand) or the application volume.

The cosmetic composition of the present invention can include, in addition to the compounds represented by formulas 1~6 of the present invention or a pharmaceutically acceptable salt thereof, any conventional ingredients generally used in cosmetics, for example such additives and carriers as stabilizers, solubilizers, vitamins, pigments and flavors, but not always limited thereto.

The cosmetic composition of the present invention can be formulated in any form that can be accepted in the art, which is exemplified by pastes, creams, gels, powders, sprays, solutions, emulsions, suspensions (anhydrous and aqueous), surfactant containing cleansings, anhydrous products (oils and glycols), masks, packs, powders, lotions, soaps, oils, powder foundations, emulsion foundations, and wax foundations, etc. Particularly, the cosmetic composition of the present invention can be prepared in the form of soft lotion (skin), nutritional lotion (milk lotion), nutritional cream, massage cream, essence, eye cream, cleansing cream, cleansing foam, cleansing water, pack, spray, or powder.

In the case that the cosmetic composition is formulated as paste, cream or gel, the proper carrier can be selected from the group consisting of animal oil, vegetable oil, wax, paraffin, starch, tracanth, cellulose derivative, polyethylene glycol, silicon, bentonite, silica, talk and zinc oxide.

In the case that the cosmetic composition is formulated as powder or spray, the proper carrier can be selected from the group consisting of lactose, talc, silica, aluminum hydroxide, calcium silicate and polyamide powder, and in particular if the composition of the present invention is formulated as spray, a propellant such as chlorofluorohydrocarbon, propane/butane or dimethyl ether can be additionally included.

In the case that the cosmetic composition is formulated as liquid or emulsion, the proper carrier can be selected from the group consisting of solvent, solubilizer and emulsifier, which is exemplified by water, ethanol, isopropanol, ethyl carbonate, ethyl acetate, benzyl alcohol, benzyl benzoate, propylene glycol, 1,3-butyl glycol oil, glycerol aliphatic ester, polyethylene glycol and fatty acid ester of sorbitan.

In the case that the cosmetic composition is formulated as suspension, the proper carrier can be selected from the group consisting of liquid diluent such as water, ethanol or propylene glycol, suspending agent such as ethoxylated isostearyl alcohol, polyoxyethylene sorbitol ester and polyoxyethylene sorbitan ester, microcrystalline cellulose, aluminum methahydroxide, bentonite, agar, and tragacanth.

In the case that the cosmetic composition is formulated as surfactant-containing cleansing, the proper carrier can be selected from the group consisting of aliphatic alcohol sulfate, aliphatic alcohol ether sulfate, sulfosuccinic monoester, isethionate, imidazolinum derivative, methyltaurate, sarcosinate, fatty acid amide ether sulfate, alkyl amidobetain, aliphatic alcohol, fatty acid glyceride, fatty acid diethanolamide, vegetable oil, lanolin derivative and ethoxylated glycerol fatty acid ester.

In addition, the present invention provides a hair tonic composition comprising one or more compounds selected from the group consisting of the compounds represented by formulas 1~6 or a pharmaceutically acceptable salt thereof as an active ingredient.

According to an example of the present invention, the compound above can be cedrol represented by formula 1, cedryl acetate represented by formula 2, alpha-cedrene represented by formula 3, methyl cedryl ketone represented by formula 4, methyl cedryl ether represented by formula 5, or cedrene epoxide represented by formula 6.

In a preferred embodiment of the present invention, the present inventors confirmed that cedrol, cedryl acetate, and alpha-cedrene exhibited the effect of promoting hair regrowth (see FIGS. 13a~13d and FIG. 20).

Therefore, the compounds represented by formulas 1~6 can be effectively used as a hair tonic composition.

The hair tonic composition of the present invention can contain the compounds represented by formulas 1~6 of the invention at the concentration of 0.001~99.99 weight % by the total weight of the hair tonic composition, and preferably at the concentration of 0.1~50 weight %. However, the concentration ratio above can be changed according to the severity of hair loss or the purpose of use as long as the concentration does not cause toxicity in a human body.

The hair tonic composition of the present invention can include, in addition to the compounds represented by formulas 1~6, any conventional ingredients generally used as pharmaceuticals or cosmetics raw materials, for example such additives as purified water, mineral water, ethanol, glycerin, squalane, 1,3-propylene glycol, 1,3-butylene glycol, castor oil, tsubaki oil, liquid petrolatum, surfactants, emulsifiers, thickeners, preservatives, antioxidants, fragrances, or carriers.

In addition to the ingredients mentioned above, the composition of the present invention can contain any ingredient that can supply nutrients to hair follicles or a hair growth promoting auxiliary component, which is exemplified by vitamins, amino acids, vegetable and animal oils, or sodium chloride. At this time, the vitamins herein can be exemplified by vitamin A, vitamin B1, vitamin B2, niacin (nicotinic acid), vitamin C, vitamin E, sodium pantothenate, potassium pantothenate, or biotin H (vitamin H). The amino acid herein can be dopa. The vegetable and animal oils herein can be exemplified by hempseed oil, egg oil, olive oil, *camellia* oil, rapeseed oil, sesame oil, or germ oil. Such auxiliary component can be added to the composition of the present invention at the concentration of 0.0001~10 weight %, preferably 0.01~1 weight % by the total weight of the composition.

The composition of the present invention can be directly applied or dispersed on hair or scalp. So, the composition can be prepared in the form of hair tonic, hair lotion, hair cream, hair spray, hair mousse, hair gel, hair conditioner, hair shampoo, hair rinse, hair pack, hair treatment, eyebrow hair growth agent, eyelash hair growth agent or eyelash nutrient, pet shampoo or pet rinse.

The composition of the present invention can be formulated in any form that can be conventionally prepared in this field, which is exemplified by cream, lotion, tonic, spray, aerosol, oil, solution, suspension, gel, ointment, emulsion, or paste.

In the case that the composition of the present invention is formulated as paste, cream or gel, the proper carrier can be selected from the group consisting of animal oil, vegetable oil, paraffin, starch, tracanth, cellulose derivative, polyethylene glycol, silicon, bentonite, silica, talk and zinc oxide.

In the case that the composition of the present invention is formulated as spray, the proper carrier can be selected from the group consisting of lactose, talc, silica, aluminum hydroxide, calcium silicate and polyamide powder, and in particular if the composition of the present invention is formulated as spray, a propellant such as chlorofluorohydrocarbon, propane/butane or dimethyl ether can be additionally included.

In the case that the composition of the present invention is formulated as liquid, the proper carrier can be selected from the group consisting of solvent, solubilizer and emulsifier, which is exemplified by water, ethanol, isopropanol, ethyl carbonate, ethyl acetate, benzyl alcohol, benzyl benzoate, propylene glycol, 1,3-butyl glycol oil, glycerol aliphatic ester, polyethylene glycol and fatty acid ester of sorbitan.

In the case that the composition of the present invention is formulated as suspension, the proper carrier can be selected from the group consisting of liquid diluent such as water, ethanol or propylene glycol; suspending agent such as ethoxylated isostearyl alcohol, polyoxyethylene sorbitol ester and polyoxyethylene sorbitan ester, microcrystalline cellulose, aluminum methahydroxide, bentonite, agar, and tragacanth.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Inhibition of IL-17A Expression by Cedrol and its Derivatives

<1-1> Investigation of IL-17A Down-Regulation by Cedrol and its Derivatives

To investigate the inhibitory effect of cedrol and its derivatives on the expression of IL-17A, IL-17 luciferase-(LUCPorter) stable reporter cell line (IMGENEX, USA, Cat No. IML-301)] was treated with cedrol (Sigma-Aldrich, USA, Cat No. 22135), cedryl acetate (Sigma-Aldrich, USA, Cat No. 45885), alpha-cedrene (Sigma-Aldrich, USA, Cat No. 22133), methyl cedryl ketone (Sigma-Aldrich, USA, Cat No. W522805), methyl cedryl ether (Sigma-Aldrich, USA, Cat No. W525405), and cedrene epoxide (Sigma-Aldrich, USA, Cat No. S528188), followed by performing IL-17A inhibition assay. The IL-17 luciferase-(LUCPorter) stable reporter cell line is the cell line that secretes IL-17, which is prepared by inserting pLightSwitch promoter vector HEK 293, the human embryonic kidney cell line, and inserting renilla luciferase in the human IL-17A target gene as a reporter gene.

Particularly, the IL-17 luciferase-(LUCPorter) stable reporter cell line was cultured in DMEM (GIBCO, USA) comprising 4.5 g/l, of glucose, 4 mM L-glutamine, 1 mM sodium pyruvate, 10% FBS, 100 μg/ml of streptomycin, 100 units/ml of penicillin, and 3 μg/ml of puromycin. The prepared cells were distributed in a 96-well plate at the density of $5 \times 10^4$ cells/well, followed by culture in a 37° C. 5% $CO_2$ incubator for 16 hours. The cultured cells were treated with 6 kinds of the compounds of the present invention at the concentration of 10, 100, or 1,000 μg/ml, followed by further culture in a 37° C. 5% $CO_2$ incubator for 6 hours. Then, LightSwitch luciferase assay solution (CAT Number LS010, Switchgear Genomics, USA) included in LightSwitch assay kit (SwitchGear Genomics, USA) was loaded to the plate (50 μl/well), followed by reaction in a dark room for 30 minutes. Then, fluorescence was measured by using the multimode Reader LB-942 (Berthold, USA) and ICE program. The results obtained from the three repeated experiments were made as mean±standard deviation, which are presented as a graph.

TABLE 2

| Compound | Conc. (μg/ml) | Inhibition of IL-17A expression (%) Experiment-1 | Experiment-2 | Experiment-3 | Average Inhibition (%) |
|---|---|---|---|---|---|
| cedrol | 0 | 0 | 0 | 0 | 0 |
| | 10 | 24 | 0 | 33 | 19.0 |
| | 100 | 21 | 14 | 43 | 26.0 |
| | 1000 | 76 | 59 | 72 | 69.0 |
| alpha-cedrene | 0 | 0 | 0 | 0 | 0 |
| | 10 | 6 | 3 | 21 | 10.0 |
| | 100 | 21 | 11 | 32 | 21.3 |
| | 1000 | 36 | 23 | 35 | 31.3 |
| cedryl acetate | 0 | 0 | 0 | 0 | 0 |
| | 10 | Experiment X | 15 | 23 | 19.0 |
| | 100 | Experiment X | 27 | 36 | 31.5 |
| | 1000 | Experiment X | 74 | 90 | 82.0 |
| methyl cedryl ketone | 0 | 0 | 0 | 0 | 0 |
| | 10 | 0 | 1 | 13 | 4.7 |
| | 100 | 12 | 15 | 25 | 17.3 |
| | 1000 | 78 | 58 | 66 | 67.3 |
| methyl cedryl ether | 0 | 0 | 0 | 0 | 0 |
| | 10 | −6 | 4 | 4 | 0.7 |
| | 100 | −5 | 5 | 8 | 2.7 |
| | 1000 | 48 | 18 | 26 | 30.7 |
| cedrene epoxide | 0 | 0 | 0 | 0 | 0 |
| | 10 | 11 | 4 | 0 | 5.0 |
| | 100 | 14 | 16 | 12 | 14.0 |
| | 1000 | 60 | 56 | 46 | 54.0 |

As a result, as shown in FIG. 1 and Table 2, the expression of IL-17A in the control group was 2,582 units. When those 6 compounds were treated at the concentration of 10, 100, or 1,000 μg/ml to experimental groups, the expression of IL-17A in the group treated with cedrol was 1,718±174 units (67% by the control), 1,460±124 units (57% by the control), and 715±45 units (28% by the control). The expression of IL-17A in the group treated with alpha-cedrene was 2,042±114 units (79% by the control), 1,757±310 units (68% by the control), and 1,688±64 units (65% by the control). The expression of IL-17A in the group treated with cedryl acetate was 1,994±304 units (77% by the control), 1,648±138 units (64% by the control), and 257±6 units (10% by the control). The expression of IL-17A in the group treated with methyl cedryl ketone was 2,248±194 units (87% by the control), 1,930±111 units (75% by the control), and 866±106 units (34% by the control). The expression of IL-17A in the group treated with methyl cedryl ether was 2,479±136 units (96% by the control), 2,379±206 units (92% by the control), and 1,921±239 units (74% by the control). The expression of IL-17A in the group treated with cedrene epoxide was 2,591±458 units (100% by the control), 2,267±806 units (88% by the control), and 1,382±87 units (54% by the control). In particular, cedrol, cedryl acetate, and alpha-cedrene suppressed the expression of IL-17A dose-dependently.

Based on the results above, cedrol, cedryl acetate, and alpha-cedrene were selected as the compounds to be used in the following experiments.

<1-2> Investigation of $IC_{50}$ Values of Cedrol and its Derivatives to IL-17A Expression To investigate $IC_{50}$ values of cedrol, cedryl acetate, alpha-cedrene, methyl cedryl ketone, methyl cedryl ether, and cedrene epoxide, the average IL-17A expression inhibition rate of each compound was calculated by applying the values obtained in Example <1-1> to the following mathematical formula 1.

$IC_{50}$ of each compound to inhibit the IL-17A expression by 50% was obtained by using the calculated values. The average IL-17A expression inhibition rate of each compound is shown in Table 2 above.

Inhibition rate (%)=100×(measured value of control−measured value of experimental group)/measured value of control [Mathematical Formula 1]

TABLE 3

| Compound | $IC_{50}$ (μg/ml) |
|---|---|
| cedrol | 726 |
| alpha-cedrene | 1,507 |
| cedryl acetate | 608 |
| methyl cedryl ketone | 841 |
| methyl cedryl ether | 1,130 |
| cedrene epoxide | 942 |

As a result, as shown in Table 3, cedryl acetate displayed the strongest IL-17A expression inhibition activity and cedrol>methyl cedryl ketone>cedrene epoxide>methyl cedryl ether>alpha-cedrene followed in that order (Table 3).

Example 2: Delayed Effect of Cedrol, Cedryl Acetate, and Alpha-Cedrene on Psoriasis Development <2-1> Preparation of Psoriasis Induced Mice To investigate the delayed effect of cedrol, cedryl acetate, and alpha-cedrene on the development of psoriasis, total 5 groups of mice were prepared (8 mice/group). First, the hair of the entire back of the 8-week-old male Balb/c mouse whose immune system was weakened was removed by using a hair clipper (Kimlaube Hair pen 325,327, Rikei, Korea). In the middle of the shaved back of the mouse, 2 mg of imiquimod (3M Health Care Limited, England) was applied in the area of 2 cm×1.5 cm and also 1,125 mg of imiquimod was applied on the right ear of the mouse every day once a day to induce psoriasis.

The mice prepared above were divided into the distilled water treated group (IMQ), the cedrol treated group (C), the cedryl acetate treated group (CA), and the alpha-cedrene treated group (CE). At this time, the mice were orally treated with distilled water at the concentration of 200 µl/mouse and cedrol or its derivatives at the concentration of 200 µl/mouse (100 mg/kg). The day when distilled water or the compound administration started was recorded as day 0 and the administration was performed once a day for a week, during which photo-recording was performed every day (FIGS. 2A~2D). In the meantime, instead of applying imiquimod, 40 mg of vaseline was applied on the back of the control group (CONT) and 22.5 mg of vaseline was applied on the right ear of the control group. And the control group was orally administered with distilled water (200 µl/mouse).

<2-2> Weight Changes in the Psoriasis Induced Mice According to the Oral Administration of Cedrol, Cedryl Acetate, and Alpha-Cedrene To compare the weight changes in the psoriasis induced mice according to the oral administration of cedrol, cedryl acetate, and alpha-cedrene of Example <2-1>, the weight of each mouse was measured at the same time every day for a week.

Figure 3:
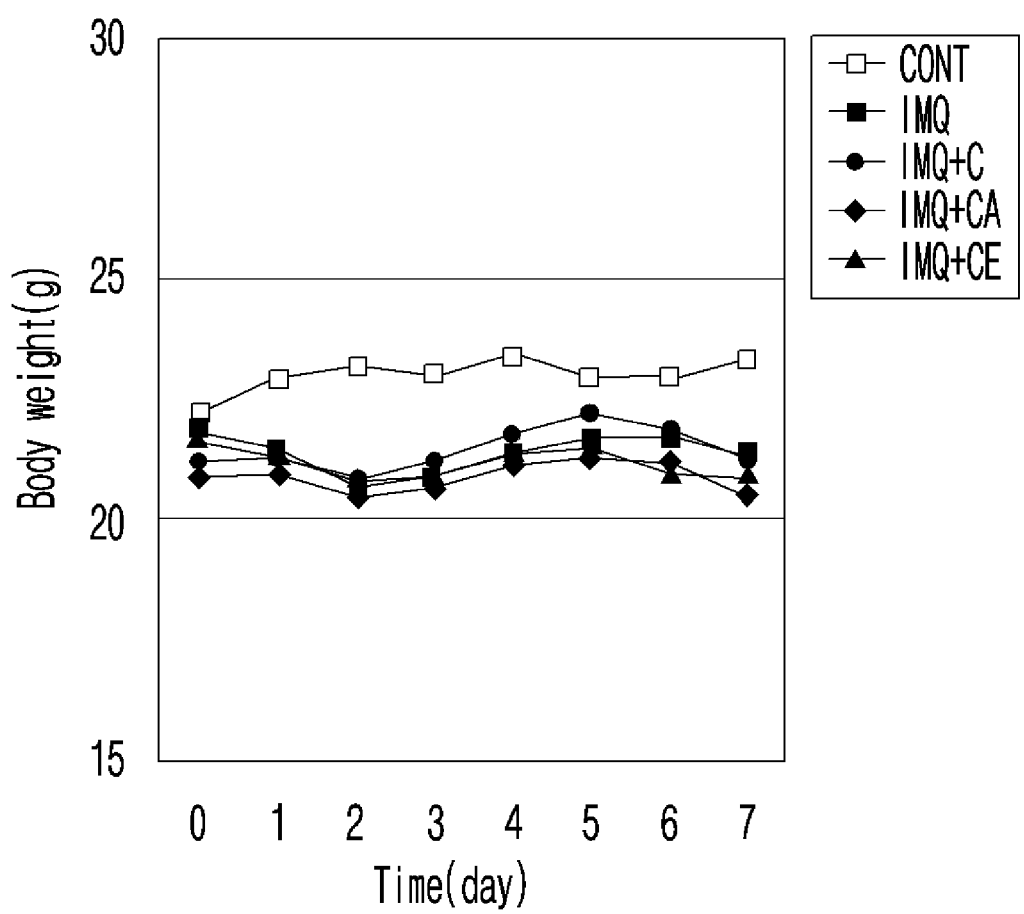
FIG. 3 is a graph illustrating the weight changes of the psoriasis induced mice orally administered with distilled water (IMQ), cedrol (IMQ+C), cedryl acetate (IMQ+CA), or alpha-cedrene (IMQ+CE) after the application of imiquimod and the non-treated control group (CONT).

As a result, as shown in FIG. 3, the weight of the control mouse (CONT) was gradually increased and increased by 1.13 g, seven days later. However, in the group treated with imiquimod (IMQ), the weight was reduced for 2 days from day 0 but reversely the weight was increased from day 3 to day 5 and once again the weight was decreased after day 5. In the group treated with IMQ alone, the weight was reduced by 0.48 g for 7 days, while the weight of the group treated with cedrol during the application of IMQ was increased by 0.025 g for 7 days (FIG. 3).

<2-3> Investigation of Ear Thickness Reduction Effect in the Psoriasis Induced Mice According to the Oral Administration of Cedrol, Cedryl Acetate, and Alpha-Cedrene The psoriasis induced mice orally administered with cedrol, cedryl acetate, and alpha-cedrene of Example <2-1> was observed with the naked eye. Then, the psoriasis area severity index (PASI) was calculated with the range of 1~4 to confirm the reduction effect of the compounds on the ear thickness.

As a result, as shown in FIGS. 2A~2D and FIG. 4, the ear thickness of the group treated with IMQ alone was increased the most. Precisely, the mean point was 0.83 on day 1, which continuously increased to 3.5 on day 7. In the group treated with cedrol after the application of IMQ, the mean ear thickness point was 2.6 on day 7. In the group treated with cedrol acetate after the application of IMQ, the mean ear thickness point was 2.3 on day 7. In the group treated with alpha-cedrene after the application of IMQ, the mean ear thickness point was 2.6 on day 7. The ear thickness reduction effect was observed in the group treated with the compounds of the present invention, among which cedryl acetate showed the strongest reduction effect, followed by alpha-cedrene and cedrol in that order (FIGS. 2A~2D and FIG. 4).

<2-4> Investigation of Keratosis Reduction Effect in the Psoriasis Induced Mice According to the Oral Administration of Cedrol, Cedryl Acetate, and Alpha-Cedrene The psoriasis induced mice orally administered with cedrol, cedryl acetate, and alpha-cedrene of Example <2-1> was observed with the naked eye. Then, the psoriasis area severity index (PASI) was calculated to confirm the reduction effect of the compounds on keratosis. Keratosis is a symptom of psoriasis. The application of IMQ can induce keratosis.

As a result, as shown in FIGS. 2A-2D and FIG. 5, keratosis was strongly induced in the group treated with IMQ alone and the mean point was 3.8 on day 7. The mean point of the group treated with cedrol after the application of IMQ was 3.00 on day 7, while the mean point of the group treated with cedryl acetate after the application of IMQ was 3.08 on day 7. The mean point of the group treated with alpha-cedrene after the application of IMQ was 2.66 on day 7. Therefore, the keratosis reduction effect was observed in those groups treated with the compounds of the invention, among which alpha-cedrene showed the strongest reduction effect, followed by cedryl acetate and cedrol in that order (FIGS. 2A~2D and FIG. 5).

<2-5> Investigation of Skin Flair Reduction Effect in the Psoriasis Induced Mice According to the Oral Administration of Cedrol, Cedryl Acetate, and Alpha-Cedrene The psoriasis induced mice orally administered with cedrol, cedryl acetate, and alpha-cedrene of Example <2-1> was observed with the naked eye. Then, the psoriasis area severity index (PASI) was calculated to confirm the reduction effect of the compounds on skin flair. Skin flair is a symptom of psoriasis. The application of IMQ can induce skin flair.

As a result, as shown in FIGS. 2A~2D and FIG. 6, skin flair was strongly induced in the group treated with IMQ alone and the mean point was 4.00 on day 7. The mean point of the group treated with cedrol after the application of IMQ was 3.33 on day 7, while the mean point of the group treated with cedryl acetate after the application of IMQ was 3.16 on day 7. The mean point of the group treated with alpha-cedrene after the application of IMQ was 3.33 on day 7. Therefore, the skin flair reduction effect was observed in those groups treated with the compounds of the invention, among which alpha-cedrene showed the strongest reduction effect, followed by cedrol and cedryl acetate in that order (FIGS. 2A~2D and FIG. 6).

<2-6> Comparison of Cumulative Score of Psoriasis Area Severity Index for Ear Thickness, Keratosis, and Skin Flair of the Psoriasis Induced Mice Orally Administered with Cedrol, Cedryl Acetate, and Alpha-Cedrene The psoriasis area severity index obtained in Examples <2-3> and <2-5> was accumulated to compare the psoriasis area severity index for ear thickness, keratosis and skin flair of the mouse groups respectively treated with cedrol, cedryl acetate, and alpha-cedrene via oral-administration.

Figure 7:
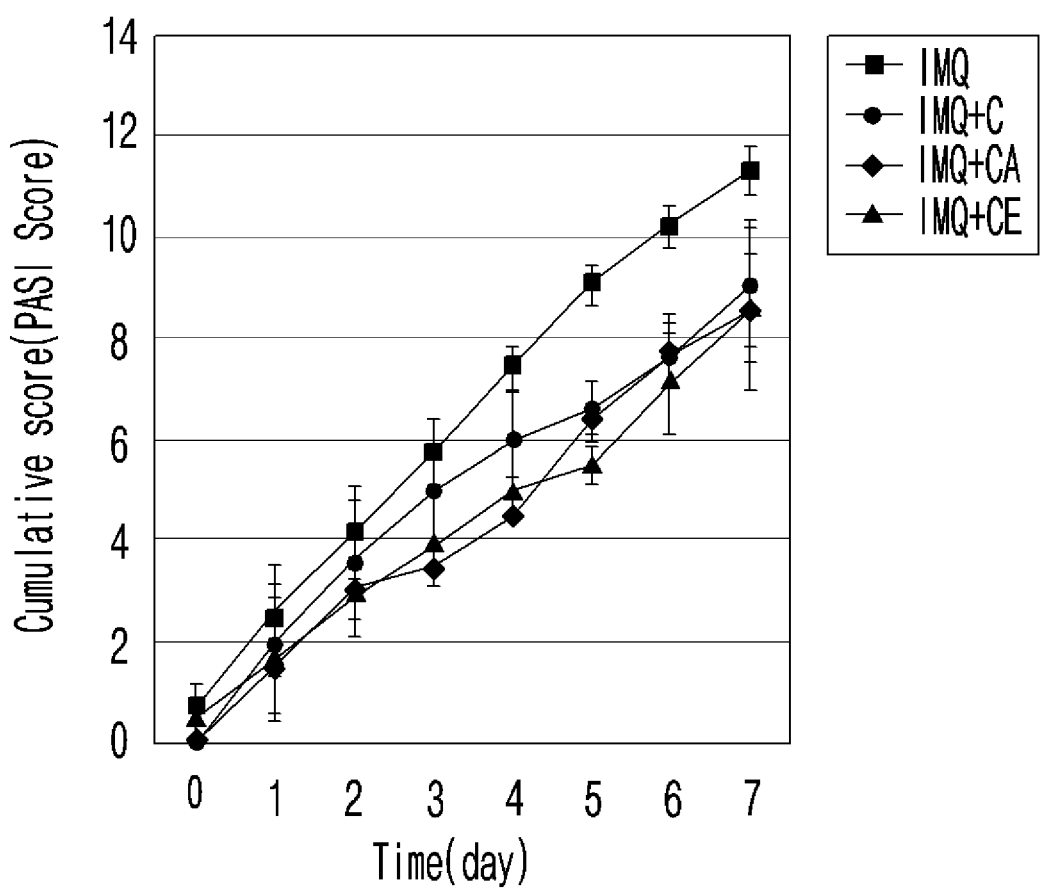
FIG. 7 is a graph illustrating the changes of the psoriasis area severity index (PASI) reflecting the ear thickness, keratosis, and skin flair in the psoriasis induced mice according to the oral administration of distilled water (IMQ), cedrol (IMQ+C), cedryl acetate (IMQ+CA), or alpha-cedrene (IMQ+CE) after the application of imiquimod.

As a result, as shown in FIG. 7, alpha-cedrene and cedryl acetate exhibited the strongest reduction effect at a similar level (FIG. 7).

<2-7> Investigation of Skin Pain Reduction Effect in the Psoriasis Induced Mice According to the Oral Administration of Cedrol, Cedryl Acetate, and Alpha-Cedrene When the back of the psoriasis induced mice orally administered with cedrol, cedryl acetate, and alpha-cedrene of Example <2-1> was pinched, those mice who sound painfully with strong rejection were counted. Skin pain is a symptom of psoriasis, and when IMQ is applied, skin pain becomes stronger as time goes by.

Figure 8:
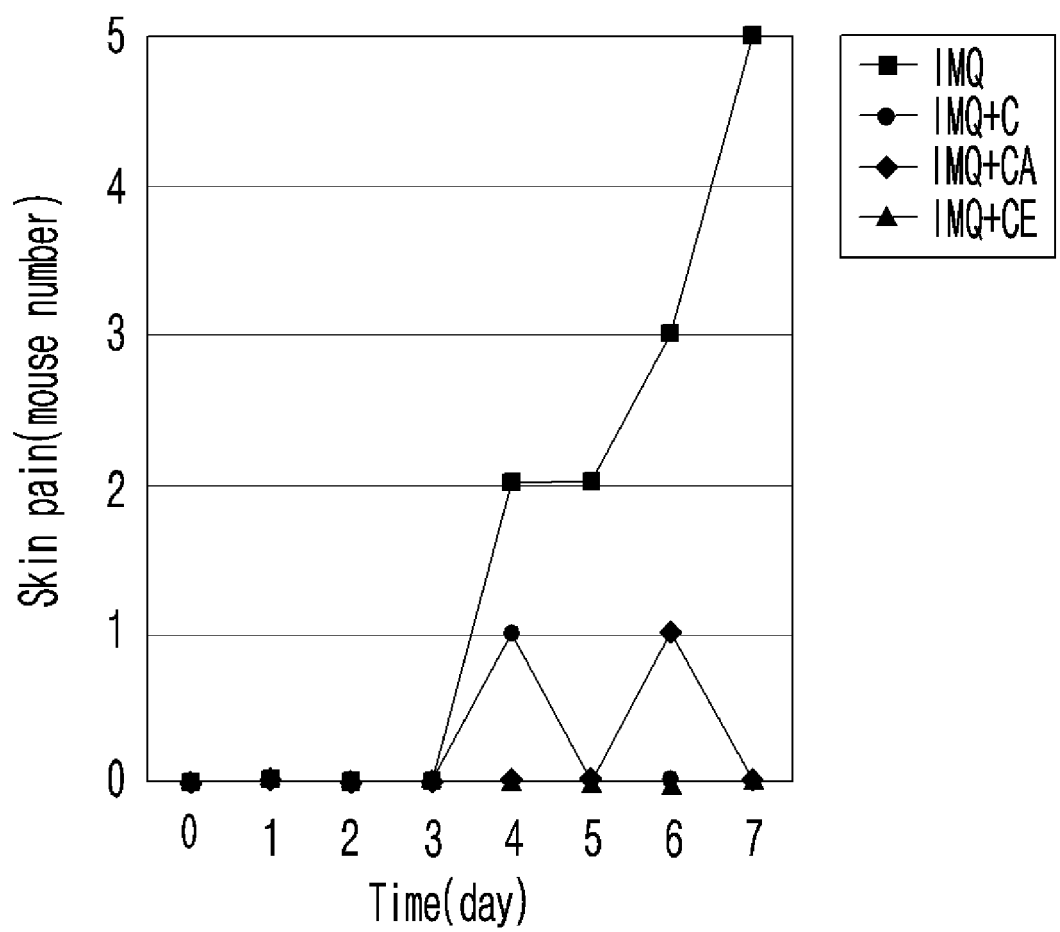
FIG. 8 is a graph illustrating the comparison of the reduction effect on skin pain of the psoriasis induced mice according to the oral administration of distilled water (IMQ), cedrol (IMQ+C), cedryl acetate (IMQ+CA), or alpha-cedrene (IMQ+CE) after the application of imiquimod.

As a result, as shown in FIG. 8, the mice in all groups showed pain from 3 days after the administration. In the group treated with IMQ alone, 5 mice were confirmed to have pain on day 7. However, in the group treated with cedrol after the application of IMQ, only one mouse showed pain on day 4 and no mice were confirmed to have pain on day 5. In the group treated with cedryl acetate after the application of IMQ, only one mouse showed pain on day 6 and no mice were confirmed to have pain on day 7. In the group treated with alpha-cedrene after the application of IMQ, no mice showed pain during the 7 day observation period. Therefore, the skin pain reduction effect was observed in those groups treated with the compounds of the invention, among which alpha-cedrene showed the strongest reduction effect, followed by cedrol and cedryl acetate in that order (FIG. 8).

<2-8> Investigation of Skin Hemorrhage Spot Reduction Effect in the Psoriasis Induced Mice According to the Oral Administration of Cedrol, Cedryl Acetate, and Alpha-Cedrene The psoriasis induced mice orally administered with cedrol, cedryl acetate, and alpha-cedrene of Example <2-1> were observed by the naked eye, and the number of mice showing hemorrhage spots was counted. Hemorrhage spot is a symptom of psoriasis, and when IMQ is applied, the number of skin hemorrhage spots increases as time goes by.

As a result, as shown in FIGS. 2A~2D and FIG. 9, only one mouse in the group treated with IMQ alone showed hemorrhage spots on day 3 and 5 mice showed hemorrhage spots on day 7. In the group treated with cedrol after the application of IMQ, one mouse showed hemorrhage spots on day 4 and 3 mice showed hemorrhage spots on day 7. In the meantime, in the group treated with cedryl acetate after the application of IMQ, one mouse showed hemorrhage spots on day 5 and one mouse showed hemorrhage spots on day 7. In the group treated with alpha-cedrene after the application of IMQ, two mice showed hemorrhage spots on day 5 and only one mouse showed hemorrhage spots on day 7. Therefore, the skin hemorrhage spot reduction effect was observed in those groups treated with the compounds of the invention, among which cedryl acetate showed the strongest reduction effect, followed by alpha-cedrene and cedrol in that order (FIGS. 2A~2D and FIG. 9).

<2-9> Investigation of Skin Wrinkle Reduction Effect in the Psoriasis Induced Mice According to the Oral Administration of Cedrol, Cedryl Acetate, and Alpha-Cedrene The psoriasis induced mice orally administered with cedrol, cedryl acetate, and alpha-cedrene of Example <2-1> were observed by the naked eye, and the number of mice showing skin wrinkles was counted. Skin wrinkle is a symptom of psoriasis, and when IMQ is applied, skin keratinization increases and accordingly skin wrinkles are formed as time goes by.

As a result, as shown in FIGS. 2A~2D and FIG. 10, only one mouse in the group treated with IMQ alone showed skin wrinkles on day 6 and 3 mice showed skin wrinkles on day 7. In the group treated with cedrol after the application of IMQ, one mouse showed skin wrinkles on day 5 and 2 mice showed skin wrinkles on day 7. In the meantime, in the group treated with cedryl acetate after the application of IMQ, one mouse showed skin wrinkles on day 5 and one mouse showed skin wrinkles on day 7. In the group treated with alpha-cedrene after the application of IMQ, one mouse showed skin wrinkles on day 6 and only one mouse showed skin wrinkles on day 7. Therefore, the skin wrinkle reduction effect was observed in those groups treated with the compounds of the invention, among which alpha-cedrene showed the strongest reduction effect, followed by cedryl acetate and cedrol in that order (FIGS. 2A~2D and FIG. 10).

<2-10> Inhibition of IL-17A Expression in the Spleen of the Psoriasis Induced Mice According to the Oral Administration of Cedrol, Cedryl Acetate, and Alpha-Cedrene The inhibition of IL-17A expression in the spleen of the psoriasis Induced mice according to the oral administration of cedrol, cedryl acetate, and alpha-cedrene was investigated by real-time PCR (polymerase chain reaction).

Particularly, the spleen was extracted from the psoriasis Induced mice orally administered with cedrol, cedryl acetate, and alpha-cedrene of Example <2-1>. Total RNA was extracted from the spleen by the conventional method. To synthesize cDNA, 2 μg of RNA was loaded in 9 μl of DEPC (RNase free water), indicating the dilution of the concentration. 1 μl of oligo dT was added thereto, followed by reaction at 70° C. for 10 minutes. The sample was treated on ice for 5 minutes, to which 2 μl of 10× reaction buffer, 2 μl of dNTP (10 mM each), 1 μl of M-MLV reverse transcriptase, and 5 μl of DNase free water were added to make the total volume of the reaction mixture 20 μl. The mixture was reacted at 42° C. for 1 hour to synthesize cDNA. The reaction mixture was heated at 72° C. for 10 minutes to remove the reverse transcriptase activity. Then, the reaction mixture was stored at −20° C. Real-time PCR was performed by using AMPIGENE qPCR 1-Step Green Kit (Enzo Life Sciences Inc, USA).

Before performing real-time PCR, each well of a 96-well plate was added with 10 μl of 2× Ampigene qPCR Green Mix Lo-Rox, 1 μl of forward primer [IL-17A forward primer: 5'-TCTCCTCTGAATGGGGTGAA-3'], and 1 μl of reverse primer [IL-17A reverse primer: 5'-CAGAG-TAGGGAGCTAAATTATCCA-3'], 2 μl of the cDNA template synthesized above, and 6 μl of distilled water (20 μl total). PCR was performed with the sample as follows; predenaturation at 95° C. for 2 minutes (polymerase activation), denaturation at 95° C. for 5 seconds, annealing/extension at 65° C. for 30 seconds, 40 cycles from denaturation to extension.

Figure 11:
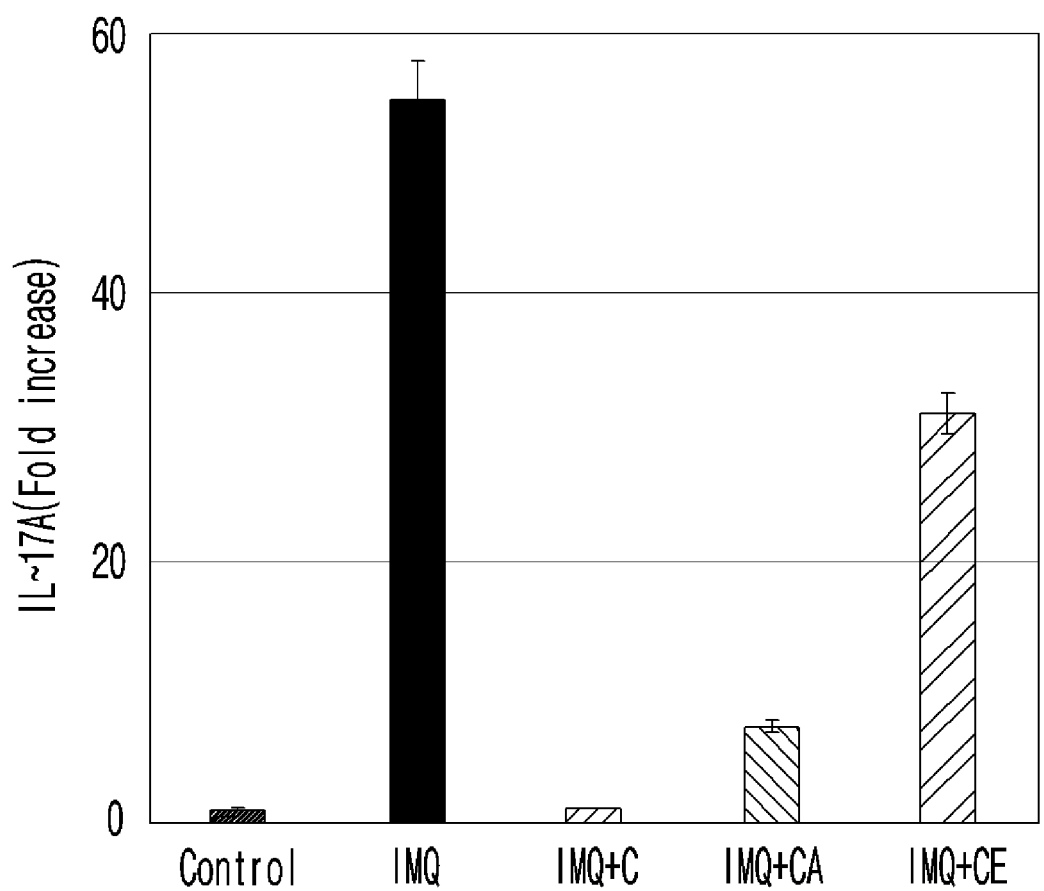
FIG. 11 is a graph illustrating the inhibitory effect on the expression of IL-17A in the spleen of the psoriasis induced mice orally administered with distilled water (IMQ), cedrol (IMQ+C), cedryl acetate (IMQ+CA), or alpha-cedrene (IMQ+CE) after the application of imiquimod and the non-treated control group (Control).

As a result, as shown in FIG. 11, when the IL-17A expression of the non-treated control group was regarded as value 1, the value of the IL-17A expression of the group treated with IMQ alone was 54.9±5.5. The IL-17A expression value of the group treated with cedrol, cedryl acetate, or alpha-cedrene after the application of IMQ was 1.1±0.1, 7.4±0.7, and 31.0±3.1, respectively. Therefore, the expression of IL-17A was inhibited in those groups treated with the compounds of the invention, among which alpha-cedrene showed the strongest inhibition effect, followed by cedryl acetate and cedrol in that order (FIG. 11).

<2-11> Comparison of Skin Thickness of the Psoriasis Induced Mice Orally Administered with Cedrol, Cedryl Acetate, and Alpha-Cedrene The skin of the psoriasis induced mice orally administered with cedrol, cedryl acetate, and alpha-cedrene of Example <2-1> was stained with hematoxyline and eosine in order to compare the skin thickness.

Particularly, the psoriasis induced mice of Example <2-1> were sacrificed with $CO_2$, from which 1 cm×1 cm portions of the back surface were obtained and placed in PBS. The tissues washed with PBS were loaded in 10% formalin, followed by fixing at room temperature for a day. The fixed tissues were washed with PBS once, followed by dehydration with 25% methanol, 50% methanol, 75% methanol, and 100% methanol for 30 minutes each. Further dehydration of those tissues was additionally performed with 100% ethanol twice for 30 minutes each; with the mixed solution comprising ethanol and xylene (1:1) for 30 minutes, and with 100% xylene twice for 30 minutes each. 4 hours before washing, the modular tissue embedding center (LEICA EG 1150H, Leica, Germany) was turned on and paraplast plus (Sigma Aldrich, Korea) was melted at 60° C., followed by washing the paraffin. The tissues were loaded in a bottle, to which the melted paraffin was poured in, followed by washing in a 60° C. warm chamber twice for one hour each. The xylene-free tissues were placed in the paraffin solution, followed by reaction in the warm chamber for a day. The tissue sections were then placed on a Peel-A-Way embedding mold (Polysciences, Taiwan) and the paraffin solution was filled to half of the mold. The tissue sections were placed on top of the Peel-A-Way embedding mold, followed by fixing. An embedding ring (Thomas Scientific, USA) was placed on the mold, which was treated with the paraffin solution to solidify the mold and the ring at 4° C. for 3 hours, followed by reaction at 4° C. for a day. The embedded tissues can be semipermanently stored at 4° C. The embedded tissues were cut by using a semi-motorized rotary microtome (LEICA RM2145 Microtome, Leica, Germany), which were suspended in a 37° C. water bath to spread the paraffin wrinkles. The straightened wrinkles were collected by using a micro silane coating slide (Muto Pure Chemicals, Japan), which were dried at 37° C. for a day. When the tissues were completely dried, they were treated with xylene twice for 5 minutes each in order to eliminate the paraffin remaining in the tissues. The tissues were further washed with the mixed solution comprising ethanol and xylene (1:1), 100% ethanol, 100% methanol, 75% methanol, and 50% methanol for 2 minutes each to stain the tissues easily. The tissues were treated with a Mayer hematoxylin solution (MHS 1-100 ML, Sigma Aldrich, Korea) at room temperature for 30 minutes, followed by washing with PBS for 10 minutes. Then, an eosin Y solution (Daejung, Korea) was treated thereto at room temperature for 1 minute to stain the tissues. Upon completion of the staining, the tissues were dehydrated with 75% methanol, 100% methanol, 100% ethanol, and the mixed solution comprising ethanol and xylene (1:1) for 10 seconds each to preserve the tissues permanently. At last, the stained tissues were treated with xylene for 2 minutes for fixing. Then, the skin thickness was measured by using NIS-Elements F (Nikon software, DS-F12-U3, Nikon, USA) program on Nikon eclipse Ti microscope (Nikon Instruments, USA) plan fluor 4×0.13.

Figure 12A:
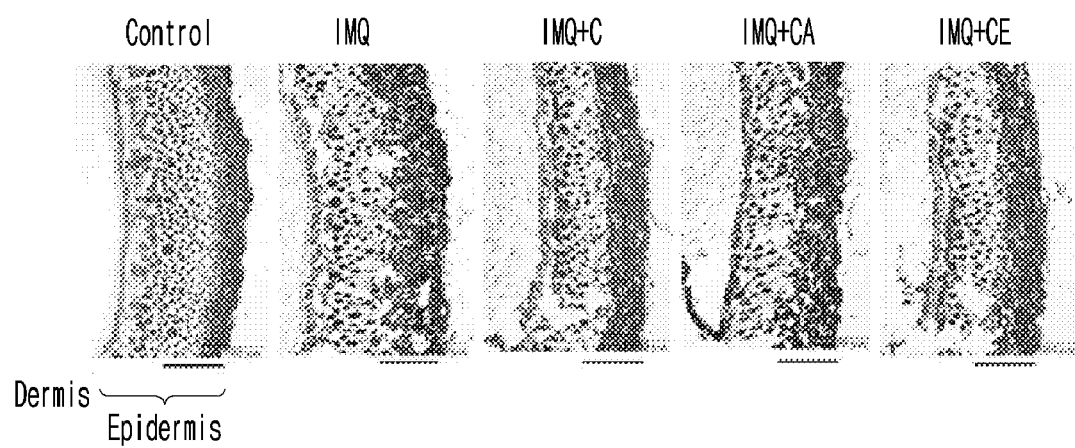
FIG. 12A is a set of photographs illustrating the skin thickness of the psoriasis induced mice orally administered with distilled water (IMQ), cedrol (IMQ+C), cedryl acetate (IMQ+CA), or alpha-cedrene (IMQ+CE) after the application of imiquimod and the non-treated control group (Control).
Figure 12B:
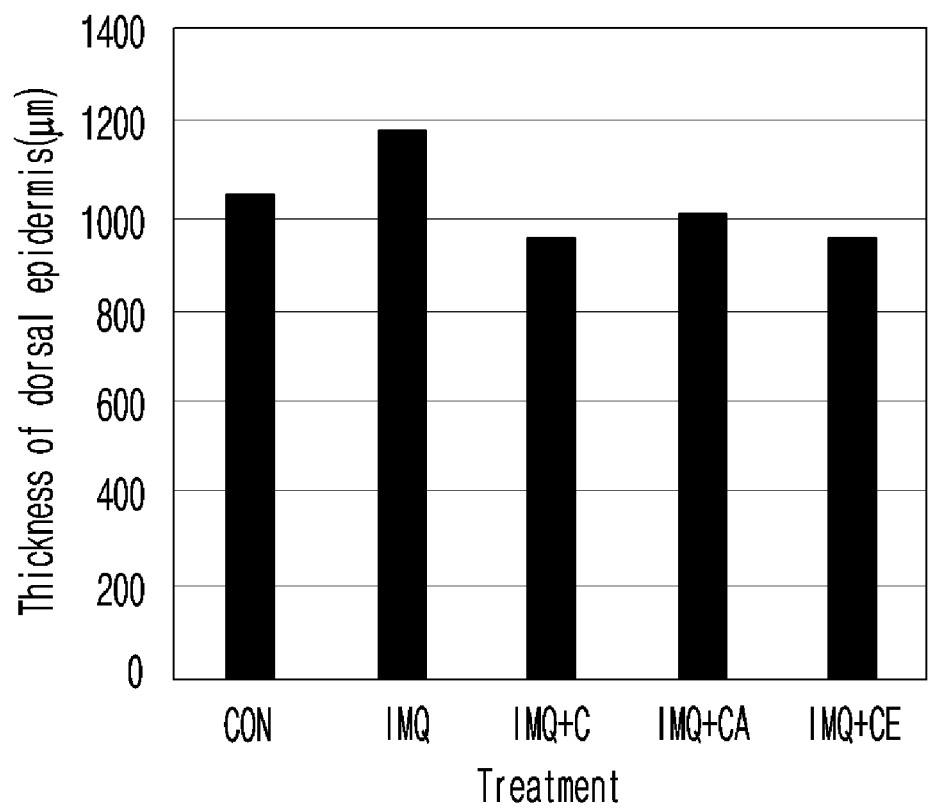
FIG. 12B is a graph illustrating the skin thickness of the psoriasis induced mice orally administered with distilled water (IMQ), cedrol (IMQ+C), cedryl acetate (IMQ+CA), or alpha-cedrene (IMQ+CE) after the application of imiquimod and the non-treated control group (Control).
Figure 13A:
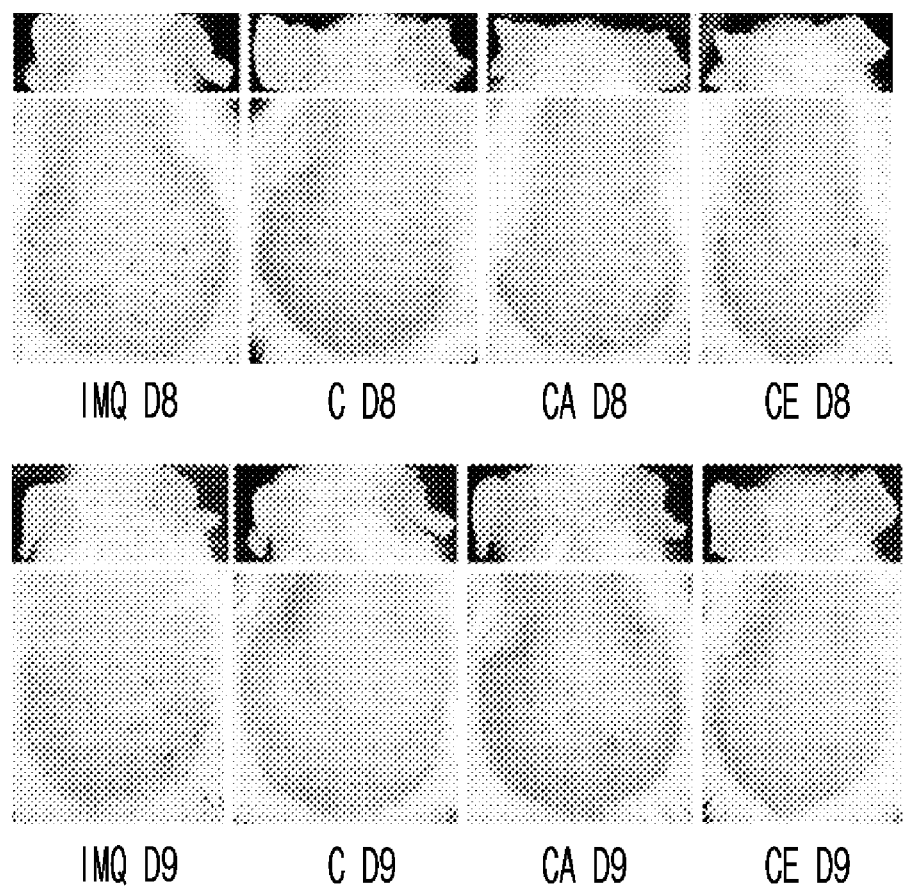
FIG. 13A is a set of photographs illustrating the therapeutic effect of distilled water (IMQ), cedrol (C), cedryl acetate (CA), or alpha-cedrene (CE) on psoriasis induced by imiquimod in the ear and the back of a mouse, observed a day after the termination of imiquimod application (D8) or two days after the termination of imiquimod application (D9) while the compound was orally administered to the mouse.
Figure 13B:
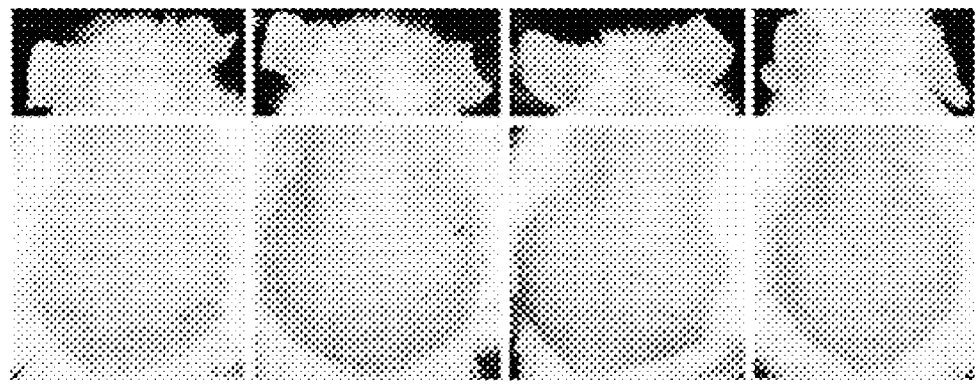
FIG. 13B is a set of photographs illustrating the therapeutic effect of distilled water (IMQ), cedrol (C), cedryl acetate (CA), or alpha-cedrene (CE) on psoriasis induced by imiquimod in the ear and the back of a mouse, observed three days after the termination of imiquimod application (D10) or four days after the termination of imiquimod application (D11) while the compound was orally administered to the mouse.
Figure 13B:
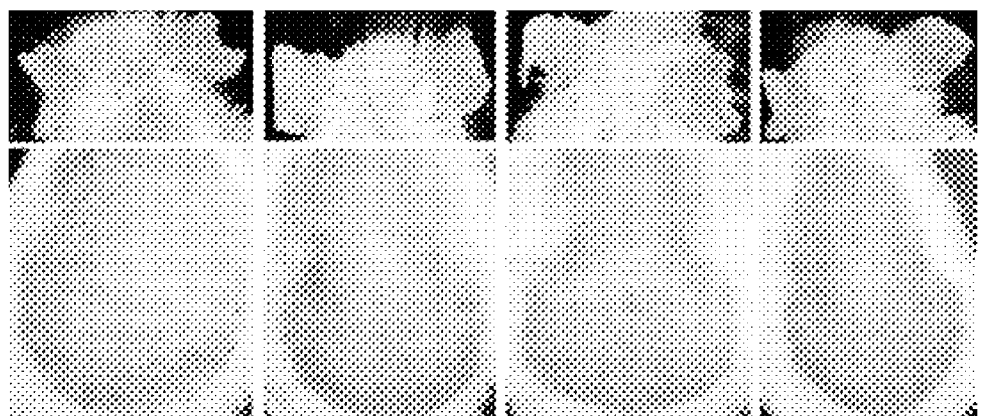
Figure 13C:
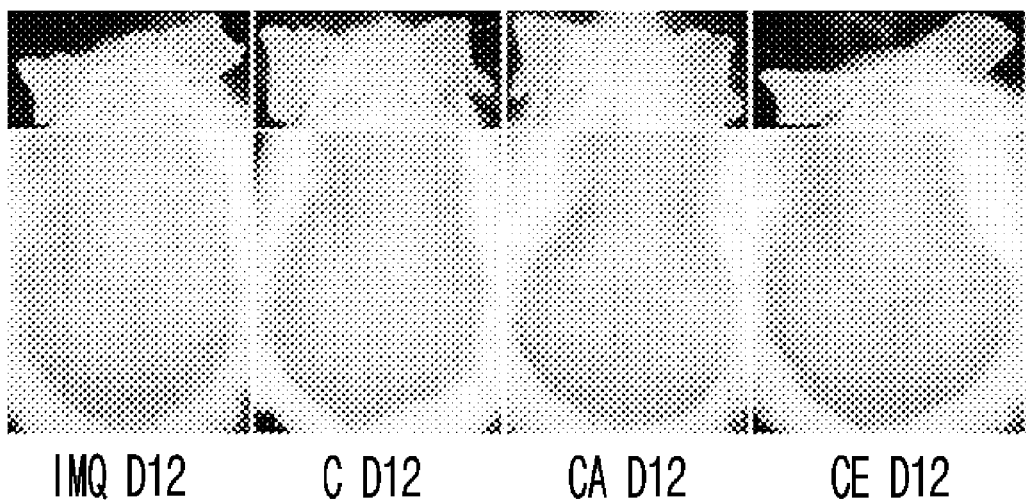
FIG. 13C is a set of photographs illustrating the therapeutic effect of distilled water (IMQ), cedrol (C), cedryl acetate (CA), or alpha-cedrene (CE) on psoriasis induced by imiquimod in the ear and the back of a mouse, observed five days after the termination of imiquimod application (D12) or six days after the termination of imiquimod application (D13) while the compound was orally administered to the mouse.
Figure 13C:
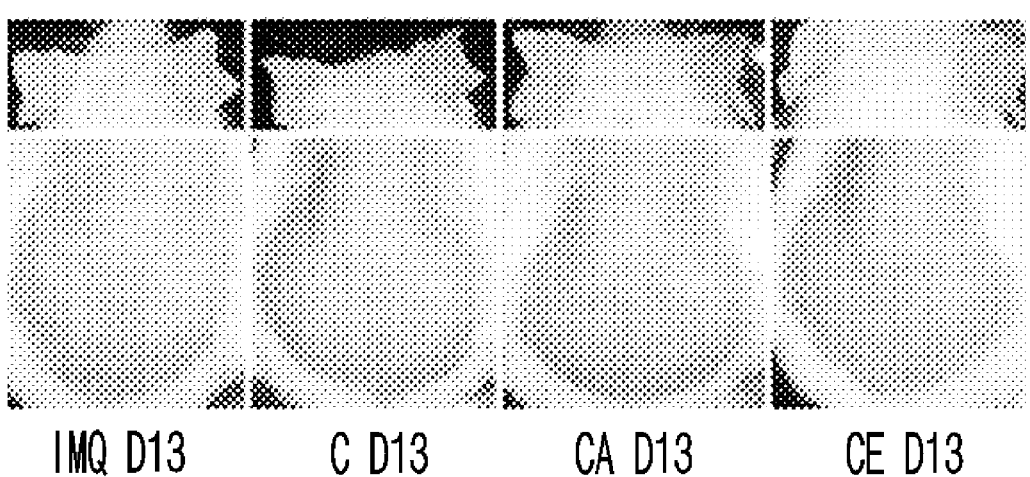
Figure 13D:
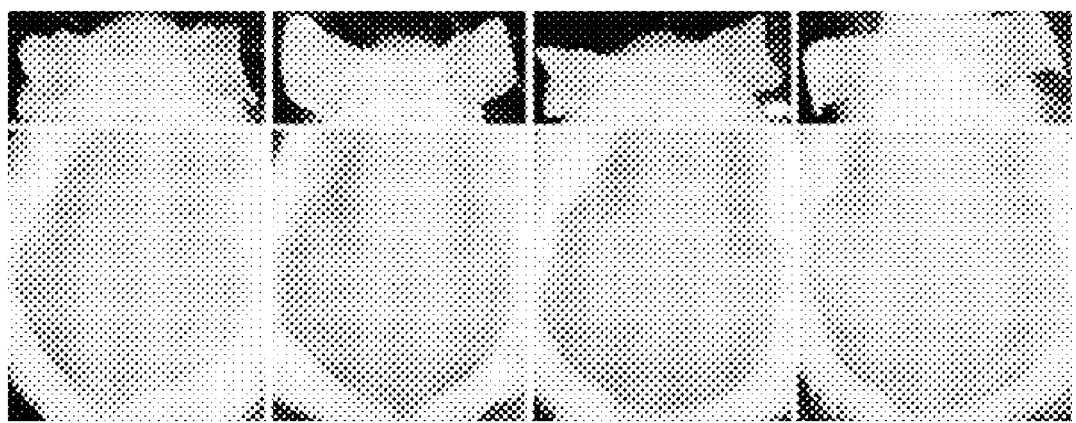
FIG. 13D is a set of photographs illustrating the therapeutic effect of distilled water (IMQ), cedrol (C), cedryl acetate (CA), or alpha-cedrene (CE) on psoriasis induced by imiquimod in the ear and the back of a mouse, observed seven days after the termination of imiquimod application (D14) or eight days after the termination of imiquimod application (D15) while the compound was orally administered to the mouse.
Figure 13D:
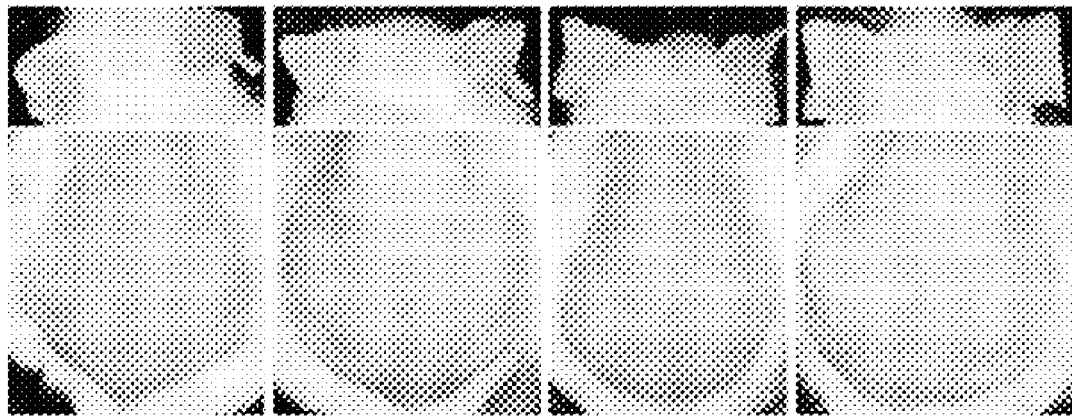

As a result, as shown in FIGS. 12A and 12B, the skin thickness of the non-treated control group and the group treated with IMQ alone was respectively 1,045 μm and 1,181 μm on day 7. The skin thickness of the group treated with cedrol, cedryl acetate, or alpha-cedrene after the application of IMQ was respectively 954 μm (19.2% inhibition), 999 μm (15.3% inhibition), and 954 μm (19.2% inhibition) on day 7. The skin thickness reduction effect was observed in the groups treated with the compounds of the invention and the effects of cedrol and alpha-cedrene were similar (FIGS. 12A and 12B).

Example 3: Confirmation of Therapeutic Effect of Cedrol, Cedryl Acetate, and Alpha-Cedrene on Psoriasis <3-1> Preparation of Psoriasis Induced Mice Imiquimod was applied to the psoriasis induced mice which had developed psoriasis for a week in Example <2-1>. The application was stopped 8 days after the application began. The groups CON and IMQ were treated with distilled water, the group C was treated with cedrol, the group CA was treated with cedryl acetate, the group CE was treated with alpha-cedrene alone at the concentration of 100 mg/kg in 200 μl, every day via oral-administration. Day 8 was the day the imiquimod application was stopped, since then the compounds were administered for 1 week once a day, during which photo-recording was performed (FIGS. 13A~13D).

<3-2> Recovery Effect of Cedrol, Cedryl Acetate, and Alpha-Cedrene on Ear Thickness of the Psoriasis Induced Mice The psoriasis induced mice orally administered with cedrol, cedryl acetate, and alpha-cedrene in Example <3-1> were observed with the naked eye. The psoriasis area severity index (Psoriasis Area Severity Index, PASI) was given from the point 1 to point 4, based on which the recovery effect on the ear thickness was evaluated.

As a result, as shown in FIGS. 13A~13D, and FIG. 14, PASI reflecting the ear thickness of the group orally administered with distilled water alone was 4.0±1.0 on day 4, and the point was maintained at average 2.0±0 from day 14 and did not decrease from that point any further. PASI reflecting the ear thickness of the group orally administered with cedrol was 4.0±0.6 on day 8, and the point was reduced to 0.7±0.6 on day 16. PASI reflecting the ear thickness of the group orally administered with cedryl acetate was 4.0±0.6 on day 8, and all 8 mice were recovered to normal from day 15. PASI reflecting the ear thickness of the group orally administered with alpha-cedrene was 4.0±0.0 on day 8, and the point was reduced to 0.7±0.6 on day 15. So, it was confirmed that the ear thickness was recovered in the groups treated with the compounds of the invention, among which cedryl acetate showed the strongest recovery effect, followed by cedrol and alpha-cedrene in that order (FIGS. 13A~13D, and FIG. 14).

<3-3> Recovery Effect of Cedrol, Cedryl Acetate, and Alpha-Cedrene on Keratosis of the Psoriasis Induced Mice The psoriasis induced mice orally administered with cedrol, cedryl acetate, and alpha-cedrene in Example <3-1> were observed with the naked eye. Then, the psoriasis area severity index (Psoriasis Area Severity Index, PASI) was calculated, based on which the recovery effect on keratosis was evaluated.

As a result, as shown in FIGS. 13A~13D, and FIG. 15, PASI reflecting keratosis of the group orally administered with distilled water alone was 4.0±1.0 on day 8, and the point was 0.7±0.6 on day 16. PASI reflecting keratosis of the group orally administered with cedrol was 3.0±0.6 on day 8, and all 8 mice were recovered to normal on day 15. PASI reflecting keratosis of the group orally administered with cedryl acetate was 4.0±0.6 on day 8, and the point was 1.0±0.0 on day 14. PASI reflecting keratosis of the group orally administered with alpha-cedrene was 4.0±0.6 on day 8, and the point was reduced to 0.3±0.6 on day 15. So, it was confirmed that keratosis was recovered in the groups treated with the compounds of the invention, among which cedrol showed the strongest recovery effect, followed by cedryl acetate and alpha-cedrene in that order (FIGS. 13A~13D, and FIG. 15).

<3-4> Recovery Effect of Cedrol, Cedryl Acetate, and Alpha-Cedrene on Skin Flair of the Psoriasis Induced Mice The psoriasis induced mice orally administered with cedrol, cedryl acetate, and alpha-cedrene in Example <3-1> were observed with the naked eye. Then, the psoriasis area severity index (Psoriasis Area Severity Index, PASI) was calculated, based on which the recovery effect on keratosis was evaluated.

As a result, as shown in FIGS. 13A~13D, and FIG. 16, PASI reflecting skin flair of the group orally administered with distilled water alone was 4.0±0.0 on day 8, and the point was 0.7±0.6 on day 16. PASI reflecting skin flair of the group orally administered with cedrol was 3.0±0.6 on day 8, and skin flair of all mice disappeared on day 16. PASI reflecting skin flair of the group orally administered with cedryl acetate was 4.0±0.0 on day 8. PASI reflecting skin flair of the group orally administered with alpha-cedrene was 4.0±1.0 on day 8, and skin flair of all mice disappeared on day 16. So, it was confirmed that skin flair was recovered in the groups treated with the compounds of the invention, among which cedrol showed the strongest recovery effect, followed by cedryl acetate and alpha-cedrene in that order (FIGS. 13A~13D, and FIG. 16).

<3-5> Comparison of Cumulative Score of Psoriasis Area Severity Index for Ear Thickness, Keratosis, and Skin Flair of the Psoriasis Induced Mice Orally Administered with Cedrol, Cedryl Acetate, and Alpha-Cedrene The psoriasis area severity index obtained in Examples <3-2> and <3-4> was accumulated to compare the psoriasis area severity index for ear thickness, keratosis and skin flair of the mouse groups respectively treated with cedrol, cedryl acetate, and alpha-cedrene via oral-administration.

Figure 17:
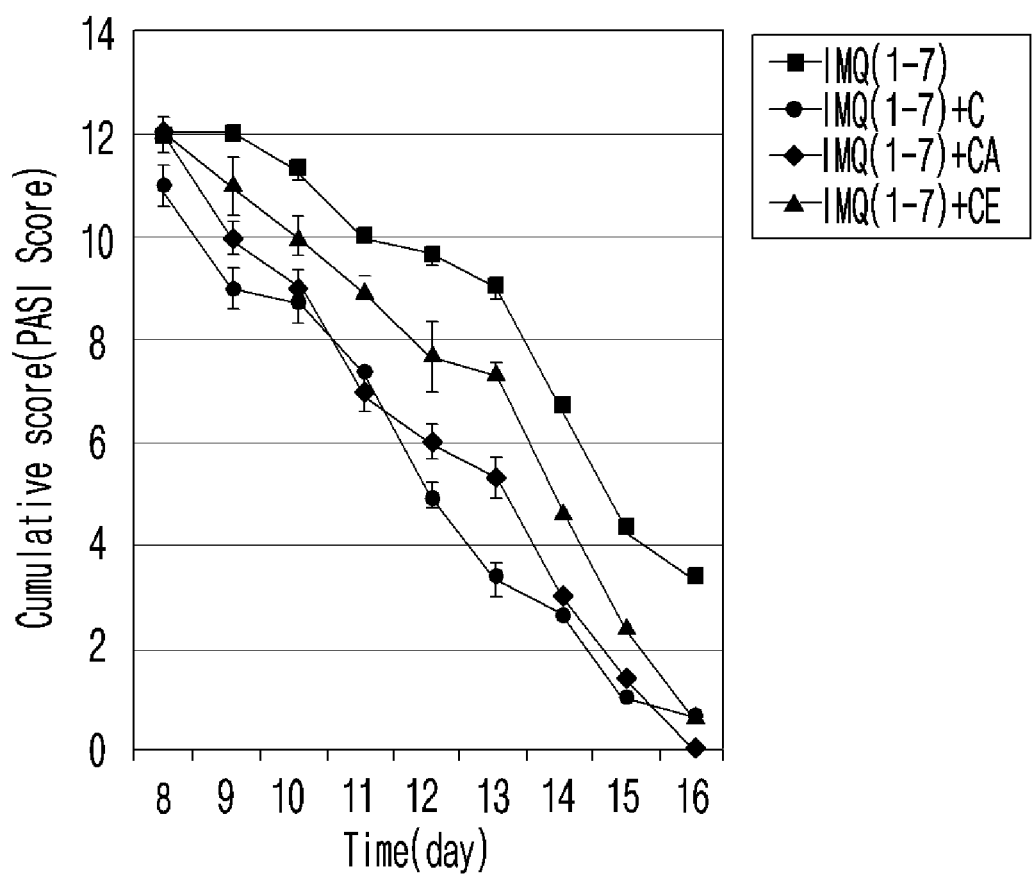
FIG. 17 is a graph illustrating the changes of the psoriasis area severity index (PASI) reflecting the ear thickness, keratosis, and skin flair in the psoriasis induced mice according to the oral administration of distilled water (IMQ(1-7)), cedrol (IMQ(1-7)+C), cedryl acetate (IMQ(1-7)+CA), or alpha-cedrene (IMQ(1-7)+CE) after the termination of imiquimod application.

As a result, as shown in FIG. 17, cedrol showed the strongest recovery effect, followed by cedryl acetate and alpha-cedrene in that order (FIG. 17).

<3-6> Recovery Effect of Cedrol, Cedryl Acetate, and Alpha-Cedrene on Hemorrhage Spots of the Psoriasis Induced Mice The psoriasis induced mice orally administered with cedrol, cedryl acetate, and alpha-cedrene of Example <3-1> were observed by the naked eye, and the number of mice showing the recovery of hemorrhage spots was counted.

As a result, as shown in FIGS. 13A~13D and FIG. 18, all 8 mice of the group orally administered with distilled water alone showed hemorrhage spots on day 8 but on day 16 when the experiment was terminated only 1 mouse showed hemorrhage spots. In the group treated with cedrol, 6 mice showed hemorrhage spots on day 8 but no mouse showed hemorrhage spots on day 12. In the group treated with cedryl acetate, 6 mice showed hemorrhage spots on day 8 but no mouse showed hemorrhage spots on day 16. In the group treated with alpha-cedrene, 4 mice showed hemorrhage spots on day 8 but no mouse showed hemorrhage spots on day 16. So, it was confirmed that the recovery effect on hemorrhage spots was confirmed in the groups treated with the compounds of the invention, among which cedrol showed the strongest recovery effect, followed by cedryl acetate and alpha-cedrene in that order (FIGS. 13A~13D and FIG. 18).

<3-7> Recovery Effect of Cedrol, Cedryl Acetate, and Alpha-Cedrene on Skin Wrinkles of the Psoriasis Induced Mice The psoriasis induced mice orally administered with cedrol, cedryl acetate, and alpha-cedrene of Example <3-1> were observed by the naked eye, and the number of mice showing the recovery of skin wrinkles was counted.

As a result, as shown in FIGS. 13A~13D and FIG. 19, 5 mice in the group orally treated with distilled water alone without being treated with the compounds of the invention showed skin wrinkles but only one mouse showed skin wrinkles on day 16 when the experiment was terminated. In the group treated with cedrol, 5 mice showed skin wrinkles on day 8 but no mouse showed skin wrinkles after day 15. In the group treated with cedryl acetate, 3 mice showed skin wrinkles on day 8 but no mouse showed skin wrinkles on day 16. In the group treated with alpha-cedrene, 3 mice showed skin wrinkles on day 8 but no mouse showed skin wrinkles on day 16. So, it was confirmed that the recovery effect on skin wrinkles was confirmed in the groups treated with the compounds of the invention, among which cedrol showed the strongest recovery effect, followed by alpha-cedrene and cedryl acetate in that order (FIGS. 13A~13D and FIG. 19).

<3-8> Accelerating Effect of Cedrol, Cedryl Acetate, and Alpha-Cedrene on Hair Regrowth of the Psoriasis Induced Mice The psoriasis induced mice orally administered with cedrol, cedryl acetate, and alpha-cedrene of Example <3-1> were observed by the naked eye, and the number of mice showing hair regrowth was counted.

As a result, as shown in FIGS. 13A~13D and FIG. 20, one mouse of the group orally treated with distilled water alone without being treated with the compounds of the invention showed hair regrowth on day 14 but 5 mice showed hair regrowth on day 16 when the experiment was terminated. In the group treated with cedrol, 2 mice showed hair regrowth on day 13 but no mouse showed skin wrinkles after day 15. In the group treated with cedrol, 2 mice showed hair regrowth on day 13 and all the mice in that group showed hair growth on day 16. In the group treated with cedryl acetate, one mouse showed hair regrowth on day 14 and 7 mice showed hair regrowth on day 16. In the group treated with alpha-cedrene, one mouse showed hair regrowth on day 13 and all the mice showed hair regrowth on day 16. So, it was confirmed that the accelerating effect on hair regrowth was confirmed in the groups treated with the compounds of the invention, among which cedrol showed the strongest accelerating effect, followed by alpha-cedrene and cedryl acetate in that order (FIGS. 13A~13D and FIG. 20).

What is claimed is:

1. A method of alleviating skin irritation in a subject, comprising:
    administering to the subject an effective amount of one or more compounds selected from the group consisting of the compounds represented by the following formulas 1~3 or a pharmaceutically acceptable salt thereof as an active ingredient,
    wherein the skin irritation is due to psoriasis; and
    wherein the skin irritation is one or more selected from the group consisting of keratosis, skin flare, skin pain and skin hemorrhage spots:

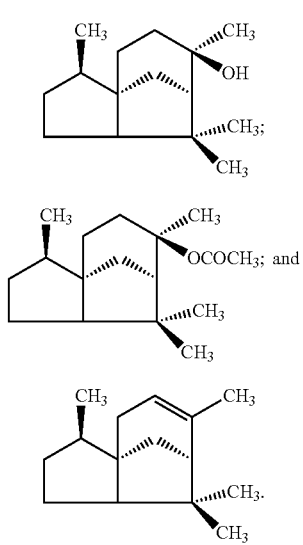
2. The method of alleviating skin irritation according to claim 1, wherein the psoriasis is mediated by interleukin-17.